(12) United States Patent
Perraut et al.

(10) Patent No.: US 11,083,379 B2
(45) Date of Patent: *Aug. 10, 2021

(54) HEALTH-MONITORING SEAT COVER

(71) Applicant: Faurecia Automotive Seating, LLC, Auburn Hills, MI (US)

(72) Inventors: John M. Perraut, Rochester Hill, MI (US); Jeffery T. Bonk, Chesterfield, MI (US)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 596 days.

This patent is subject to a terminal disclaimer.

(21) Appl. No.: 15/863,129

(22) Filed: Jan. 5, 2018

(65) Prior Publication Data

US 2019/0038229 A1 Feb. 7, 2019

Related U.S. Application Data

(60) Provisional application No. 62/540,133, filed on Aug. 2, 2017.

(51) Int. Cl.
*A61B 5/0205* (2006.01)
*B60N 2/00* (2006.01)
(Continued)

(52) U.S. Cl.
CPC ........ *A61B 5/02055* (2013.01); *A61B 5/0205* (2013.01); *A61B 5/4836* (2013.01);
(Continued)

(58) Field of Classification Search
CPC .............. A61H 7/00–002; A61H 7/004; A61H 7/007–008; A61H 2007/009; A61H 9/00–0007; A61H 9/005; A61H 9/0092; A61H 15/00–02; A61H 2201/02–0285; A61H 2201/103; A61B 5/02055; A61B 5/0205; A61B 5/4836; A61B 5/6893; A61B 5/021; A61B 5/024; A61B 5/742;
(Continued)

(56) References Cited

U.S. PATENT DOCUMENTS 3,580,245 A * 5/1971 Dill .................. A47C 7/467
  601/57
4,031,579 A * 6/1977 Larned ............... B64D 11/0619
  5/652.1

(Continued)

FOREIGN PATENT DOCUMENTS

CN     1572575      2/2005
CN     1956680 A    5/2007
(Continued)

OTHER PUBLICATIONS

Chinese Rejection Decision for Chinese App. No. 201380064313.2 sent on May 17, 2018, 3376 CN, 13 pages.
(Continued)

*Primary Examiner* — Rachel T Sippel
*Assistant Examiner* — Kelsey E Baller
(74) *Attorney, Agent, or Firm* — Barnes & Thornburg LLP

(57) ABSTRACT

An occupant support includes a seat and a seat cover. The seat is adapted to support an occupant resting thereon. The seat cover is coupled to the seat and arranged to lie between the occupant and the seat.

15 Claims, 12 Drawing Sheets

(51) Int. Cl.
| | |
|---|---|
| *B60N 2/56* | (2006.01) |
| *B60N 2/90* | (2018.01) |
| *A61B 5/00* | (2006.01) |
| *A61F 7/00* | (2006.01) |
| *A61F 7/08* | (2006.01) |
| *A61H 9/00* | (2006.01) |
| *B60N 2/60* | (2006.01) |
| *B60N 2/66* | (2006.01) |
| *B60N 2/58* | (2006.01) |
| *A61B 5/021* | (2006.01) |
| *A61B 5/024* | (2006.01) |
| *A61B 5/08* | (2006.01) |

(52) U.S. Cl.
CPC .......... *A61B 5/6892* (2013.01); *A61B 5/6893* (2013.01); *A61F 7/007* (2013.01); *A61F 7/08* (2013.01); *A61H 9/0078* (2013.01); *B60N 2/002* (2013.01); *B60N 2/5642* (2013.01); *B60N 2/5678* (2013.01); *B60N 2/5685* (2013.01); *B60N 2/60* (2013.01); *B60N 2/914* (2018.02); *B60N 2/976* (2018.02); *A61B 5/021* (2013.01); *A61B 5/024* (2013.01); *A61B 5/0816* (2013.01); *A61B 5/742* (2013.01); *A61B 2503/22* (2013.01); *A61H 2201/0103* (2013.01); *A61H 2201/0149* (2013.01); *A61H 2201/0157* (2013.01); *A61H 2201/0207* (2013.01); *A61H 2201/0221* (2013.01); *A61H 2201/1207* (2013.01); *A61H 2201/1409* (2013.01); *A61H 2201/1623* (2013.01); *A61H 2201/1633* (2013.01); *A61H 2201/1645* (2013.01); *A61H 2201/5025* (2013.01); *A61H 2201/5035* (2013.01); *A61H 2201/5043* (2013.01); *A61H 2201/5048* (2013.01); *A61H 2201/5058* (2013.01); *A61H 2201/5071* (2013.01); *A61H 2201/5082* (2013.01); *A61H 2201/5097* (2013.01); *A61H 2203/0425* (2013.01); *A61H 2230/065* (2013.01); *A61H 2230/305* (2013.01); *A61H 2230/425* (2013.01); *A61H 2230/505* (2013.01); *B60N 2/58* (2013.01); *B60N 2/665* (2015.04)

(58) Field of Classification Search
CPC .......... B60N 2/56; B60N 2/976; B60N 2/914; B60N 2/002; B60N 2/5678; B60N 2/5685; B60N 2/60; B60N 2/665; B60N 2/58
USPC ..... 297/217.3, 219.1, 452.42, 284.5; 601/84, 601/48–49
See application file for complete search history.

(56) References Cited

U.S. PATENT DOCUMENTS

| | | | | |
|---|---|---|---|---|
| 4,655,505 A * | 4/1987 | Kashiwamura | ........ | A47C 7/467 297/284.6 |
| 4,707,027 A | 11/1987 | Horvath | | |
| 4,840,425 A * | 6/1989 | Noble | ........ | A47C 7/467 297/284.1 |
| 4,928,090 A | 5/1990 | Yoshimi | | |
| 5,069,214 A | 12/1991 | Samaras | | |
| 5,155,685 A * | 10/1992 | Kishi | ........ | B60N 2/914 701/49 |
| 5,462,515 A * | 10/1995 | Tseng | ........ | A61H 7/001 5/915 |
| 6,055,473 A * | 4/2000 | Zwolinski | ........ | B60N 2/002 701/49 |
| 6,087,942 A * | 7/2000 | Sleichter, III | ........ | B60N 2/56 340/576 |
| 6,120,468 A | 9/2000 | Tseng | | |
| 6,212,719 B1 * | 4/2001 | Thomas | ........ | A47C 4/54 297/284.6 |
| 6,273,810 B1 * | 8/2001 | Rhodes, Jr. | ........ | A47C 4/54 454/120 |
| 6,422,087 B1 | 7/2002 | Potter | | |
| 7,206,631 B2 | 4/2007 | Kawachi | | |
| 7,239,945 B2 | 7/2007 | Hiemer | | |
| 7,322,652 B1 | 1/2008 | Tache | | |
| 7,774,052 B2 | 8/2010 | Burton | | |
| 7,862,113 B2 * | 1/2011 | Knoll | ........ | B60N 2/5635 297/180.14 |
| 8,123,290 B1 * | 2/2012 | Aiken | ........ | A47C 31/11 297/180.1 |
| 8,181,292 B1 | 5/2012 | Pellettiere | | |
| 8,328,279 B2 * | 12/2012 | Brncick | ........ | B60N 2/5816 297/228.11 |
| 8,430,817 B1 | 4/2013 | Al-Ali | | |
| 8,616,654 B2 | 12/2013 | Zenk | | |
| 8,672,411 B2 * | 3/2014 | Gomes | ........ | B60N 2/5635 297/452.46 |
| 8,725,311 B1 | 5/2014 | Breed | | |
| 8,757,726 B2 * | 6/2014 | Oota | ........ | B60N 2/7094 297/452.42 |
| 8,919,874 B2 * | 12/2014 | Ota | ........ | B60N 2/5642 297/180.13 |
| 9,135,803 B1 | 9/2015 | Fields | | |
| 9,440,657 B1 | 9/2016 | Fields | | |
| 9,475,389 B1 | 10/2016 | Fung | | |
| 9,505,402 B2 | 11/2016 | Fung | | |
| 9,717,345 B1 | 8/2017 | Caruso | | |
| 9,771,003 B2 | 9/2017 | Kolich | | |
| 9,848,814 B2 * | 12/2017 | Benson | ........ | A61M 21/02 |
| 10,179,525 B2 * | 1/2019 | Arata | ........ | B60N 2/5635 |
| 10,235,859 B1 | 3/2019 | Hiles | | |
| 10,258,535 B2 | 4/2019 | Lem | | |
| 10,471,864 B1 * | 11/2019 | Tait | ........ | B60N 2/565 |
| 2002/0091473 A1 | 7/2002 | Gardner | | |
| 2004/0243368 A1 | 12/2004 | Hiemer | | |
| 2005/0027416 A1 | 2/2005 | Basir | | |
| 2005/0124864 A1 | 6/2005 | MacK | | |
| 2005/0248184 A1 | 11/2005 | Piffaretti | | |
| 2006/0025698 A1 | 2/2006 | Nakagawa | | |
| 2006/0068693 A1 | 3/2006 | Kono | | |
| 2006/0175877 A1 | 8/2006 | Alionte | | |
| 2007/0029862 A1 * | 2/2007 | Bargheer | ........ | B60N 2/879 297/452.42 |
| 2007/0251749 A1 | 11/2007 | Breed | | |
| 2008/0296946 A1 | 12/2008 | Reynolds | | |
| 2009/0030576 A1 | 1/2009 | Periot | | |
| 2009/0164241 A1 | 6/2009 | Racioppo | | |
| 2010/0185068 A1 | 7/2010 | Park | | |
| 2010/0229181 A1 | 9/2010 | Ahuja | | |
| 2011/0015468 A1 | 1/2011 | Aarts | | |
| 2011/0066292 A1 | 3/2011 | Moriya | | |
| 2011/0133755 A1 | 6/2011 | Griffin | | |
| 2011/0156453 A1 * | 6/2011 | Matsushima | ........ | B60N 2/5825 297/180.12 |
| 2011/0186560 A1 * | 8/2011 | Kennedy | ........ | B60N 2/5678 219/217 |
| 2011/0304465 A1 | 12/2011 | Boult | | |
| 2012/0078123 A1 | 3/2012 | Futatsuyama | | |
| 2012/0212353 A1 | 8/2012 | Fung | | |
| 2013/0070043 A1 | 3/2013 | Geva | | |
| 2014/0031703 A1 | 1/2014 | Rayner | | |
| 2014/0039330 A1 | 2/2014 | Seo | | |
| 2014/0228649 A1 | 8/2014 | Rayner | | |
| 2014/0240132 A1 | 8/2014 | Bychkov | | |
| 2014/0276112 A1 | 9/2014 | Fung | | |
| 2015/0008710 A1 | 1/2015 | Young | | |
| 2015/0051526 A1 | 2/2015 | Wang | | |
| 2015/0151658 A1 | 6/2015 | Burris | | |
| 2015/0231991 A1 | 8/2015 | Yetukuri | | |
| 2015/0239321 A1 * | 8/2015 | Muller | ........ | G01N 19/10 297/180.1 |
| 2015/0313475 A1 | 11/2015 | Benson | | |
| 2016/0001781 A1 | 1/2016 | Fung | | |
| 2016/0019813 A1 | 1/2016 | Mullen | | |

(56) References Cited

U.S. PATENT DOCUMENTS

| | | | |
|---|---|---|---|
| 2016/0029940 A1 | 2/2016 | Iizuka | |
| 2016/0086500 A1 | 3/2016 | Kaleal, III | |
| 2016/0339801 A1 | 11/2016 | Pereny | |
| 2016/0339802 A1 | 11/2016 | Hanlon | |
| 2017/0136842 A1 | 5/2017 | Anderson | |
| 2017/0136922 A1 | 5/2017 | Von Ballmoos | |
| 2017/0158202 A1 | 6/2017 | Yang | |
| 2017/0282930 A1 | 10/2017 | Kochhar | |
| 2017/0285641 A1 | 10/2017 | Goldman-Shenhar | |
| 2017/0312534 A1 | 11/2017 | Cao | |
| 2017/0326013 A1 | 11/2017 | Hyde | |
| 2017/0340214 A1 | 11/2017 | Benson | |
| 2018/0037236 A1 | 2/2018 | Yamaguchi | |
| 2018/0178808 A1 | 6/2018 | Zhao | |
| 2018/0229674 A1 | 8/2018 | Heinrich | |

FOREIGN PATENT DOCUMENTS

| | | | |
|---|---|---|---|
| CN | 103565429 A | 2/2014 | |
| CN | 104837403 A | 8/2015 | |
| CN | 0104875744 | 9/2015 | |
| DE | 102005038289 | 3/2007 | |
| DE | 102007053119 | 5/2009 | |
| DE | 102009021532 | 11/2010 | |
| EP | 1447070 A1 * | 8/2004 | ........... B60N 2/5685 |
| JP | 2010264092 | 11/2010 | |
| KR | 1020010061858 | 7/2001 | |
| KR | 1020140027641 | 3/2014 | |
| KR | 0101642697 | 8/2016 | |
| WO | 2013109154 | 7/2013 | |
| WO | 2013109154 A1 | 7/2013 | |
| WO | 2014147828 | 9/2014 | |
| WO | 02014147828 | 9/2014 | |
| WO | 2015127193 | 8/2015 | |
| WO | 2015200224 | 12/2015 | |
| WO | 2016070981 | 5/2016 | |

OTHER PUBLICATIONS

PCT International Search Report and Written Opinion completed by the ISA/US dated Apr. 22, 2014 and issued in connection with PCT/US2013/071620.
Chinese Office Action for Chinese App. No. 201380064313.2 dated Apr. 12, 2017, 3376 CN, 21 pages.
PCT Search Report and Written Opinion completed by the ISA/EP dated May 21, 2015 and issued in connection with PCT/US2015/016803, 13 pages.
Chinese Office Action for Chinese App. No. 201380064313.2 dated Sep. 28, 2017, 3376 CN, 19 pages.
Office Action dated Nov. 29, 2017 for U.S. Appl. No. 15/235,882; (pp. 1-7).
European Examination Report for European App. No. 15 707 235.6 dated Feb. 6, 2018, 3619 EP, 7 pages.
Chinese Office Action for Chinese App. No. 201710799929.9 dated Sep. 27, 2019, 4112 CN, 14 pages.
Office Action dated Oct. 29, 2019 for U.S. Appl. No. 15/692,396, 4112 US-U (pp. 1-37).
Office Action dated May 1, 2019 for U.S. Appl. No. 15/692,396, 4112 US-U (pp. 1-27).
Office Action dated May 16, 2019 for U.S. Appl. No. 15/626,525, 4081 US-U (pp. 1-12).
Office Action dated Sep. 3, 2019 for U.S Appl. No. 15/613,578, 4078 US-U, (pp. 1-20).
Chinese Office Action for Chinese Pat. App. No. 201580011844.9 dated Nov. 19, 2619, 3619 CN, 13 pages, (brief summary included in English).
Office Action dated Mar. 4, 2020 fo U.S. Appl. No. 15/678,710, 3376 US-U, (pp. 1-14).
Chinese Office Action for Chinese Pat. App. No. 201580011844.9 dated Jul. 12, 2019, 3619 CN, 13 pages, (brief summary included in English).
Chinese Office Action for Chinese Pat. App. No. 201580011844.9 dated Mar. 14, 2019, 3619 CN, 12 pages, (brief summary included in English).
Chinese Office Action for Chinese Pat. App. No. 201580011844.9 dated Aug. 28, 2018, 3619 CN, 19 pages, (brief summary included in English).
N. Mizuno and K. Washino, "A model based filtering technique for driver's heart rate monitoring using seat-embedded vibration sensors," 2014 6th International Symposium on Communications, Control and Signal Processing (ISCCSP), Athens, 2014, pp. 137-140, doi: 10.1109/ISCCSP.2014.6877834. (Year: 2014).
Second Chinese Office Action for Chinese App. No. 201710799929.9 dated Jul. 1, 2020, 4112 CN, 6 pages.
Fifth Chinese Office Action for Chinese Pat. App. No. 201580011844.9 dated Mar. 13, 2020, 3619 CN, 13 pages, (brief summary included in English).
Choi et al., "Noninvaisive cuffless blood pressure estimation usingpulse transit time and Hilbert-Huang transform," Computers and Electridal Engineering Journal, 39, 103-111 (Nov. 8, 2012), 9 pages.
Wong et al., "The Effects of Exercises on teh Relationship between Pulse Transit Time and Arterial Blood Pressure," Proceedings of the 2005 IEEE Enginering in Medicine and Biology 27th Annual Conference, Shanghai, China , Sep. 1-4, 2005, 3 pages.
Office Action dated Apr. 27, 2020 for U.S. Appl. No. 15/626,525, 4081 US-U (pp. 1-11).
Office Action dated Apr. 30, 2020 for U.S. Appl. No. 15/873,034, 4296 US-U (pp. 1-24).
European Examination Report for European App. No. 15 707 235.6 dated Apr. 15, 2020, 3619 EP, 5 pages.
Office Action dated May 8, 2020 for U.S. Appl. No. 15/613,578, 4078 US-U (pp. 1-23).
Office Action dated Sep. 24, 2020 for U.S. Appl. No. 15/626,525, 4081 US-U (pp. 1-10).
Office Action dated Sep. 3, 2020 for U.S. Appl. No. 15/873,034, 4296 US-CON1 (pp. 1-17).
Office Action dated Feb. 1, 2021 for U.S. Appl. No. 15/873,034, 4296 US-CON1 (pp. 1-19).

* cited by examiner

HEALTH-MONITORING SEAT COVER

PRIORITY CLAIM

This application claims priority under 35 U.S.C. § 119(e) to U.S. Provisional Application Ser. No. 62/540,133, filed Aug. 2, 2017, which is expressly incorporated by reference herein.

BACKGROUND

The present disclosure relates to covers adapted for use with occupant supports. More particularly, the present disclosure relates to covers configured to couple removably to occupant supports.

SUMMARY

According to the present disclosure, an occupant support includes a seat and a seat cover. The seat is adapted to support an occupant resting thereon. The seat cover is couple to the seat and arranged to lie between the occupant and the seat.

In illustrative embodiments, the seat cover is a health-monitoring cover. The health monitoring cover is adapted to couple removably to a seat. The health-monitoring cover includes a comfort unit configured to support an occupant of the occupant support. The health-monitoring cover may be obtained separately from the seat and used with multiple occupant supports.

In illustrative embodiments, the health-monitoring cover includes a sensor system and a control system. The sensor system is configured to obtain occupant-body signals associated with physiological characteristics of the occupant of the occupant support. The control system is configured to receive and process the occupant-body signals to determine occupant health data and occupant state data such as, for example, comfort and stress. The control system analyzes the data to recommend activating therapy systems and lifestyle amenities to improve the comfort and wellbeing of the occupant.

In illustrative embodiments, the health-monitoring cover includes a plurality of therapy systems integrated into the comfort unit and configured to provide relief the occupant. The control system is configured to monitor the occupant and the therapy systems to determine the effect of activating the therapy systems and the lifestyle amenities and to learn the occupant's preferences.

In illustrative embodiments, the occupant health data, occupant state data, and learned occupant behaviors are associated in a unique occupant data profile associated with a single occupant. The control system adds information and trends to the unique occupant data profile over time to improve its occupant comfort and wellness recommendations.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which:

FIG. 1 is a perspective and diagrammatic view of a health-monitoring cover in accordance with the present disclosure removeably coupled to an occupant support suggesting that the health-monitoring cover includes a comfort unit for supporting an occupant, a sensor system including a plurality of sensors configured to measure physiological data of an occupant positioned on top of the health-monitoring cover, and a control system removeably coupled to the back of the occupant support and configured to communicate with multiple smart devices to receive health and comfort data of the occupant;

FIG. 2 is a diagrammatic view of the health-monitoring cover of FIG. 1 showing that the health-monitoring cover includes the sensor system and the control system, the sensor system is configured to detect one or more of occupant physiological signals and environmental signals and the control system is configured to analyze the signals to generate occupant health data, occupant state data, and recommendations to improve a wellness and/or comfort of the occupant based on the occupant health data and/or the occupant state data;

FIG. 3 is a diagrammatic view of the sensor system included in the occupant support system and a plurality of experience levels of the occupant that may be determined by the control system based on the signals received from the sensor system;

FIG. 4 is a perspective and diagrammatic view of the health-monitoring cover removeably coupled to the occupant support showing that the health-monitoring cover includes a bottom cover removeably coupled to a seat bottom of the occupant support and a back cover that extends upwardly away from the bottom cover of the health-monitoring cover, and further showing portions of the health-monitoring cover broken away to reveal that the bottom cover and back cover include the comfort unit that includes an inner layer and an outer layer arranged over the inner layer, the sensor system located between the inner layer and the outer layer, a plurality of therapy systems integrated with the comfort unit, and the control system located on the back of the occupant support;

DETAILED DESCRIPTION

Figure 1:
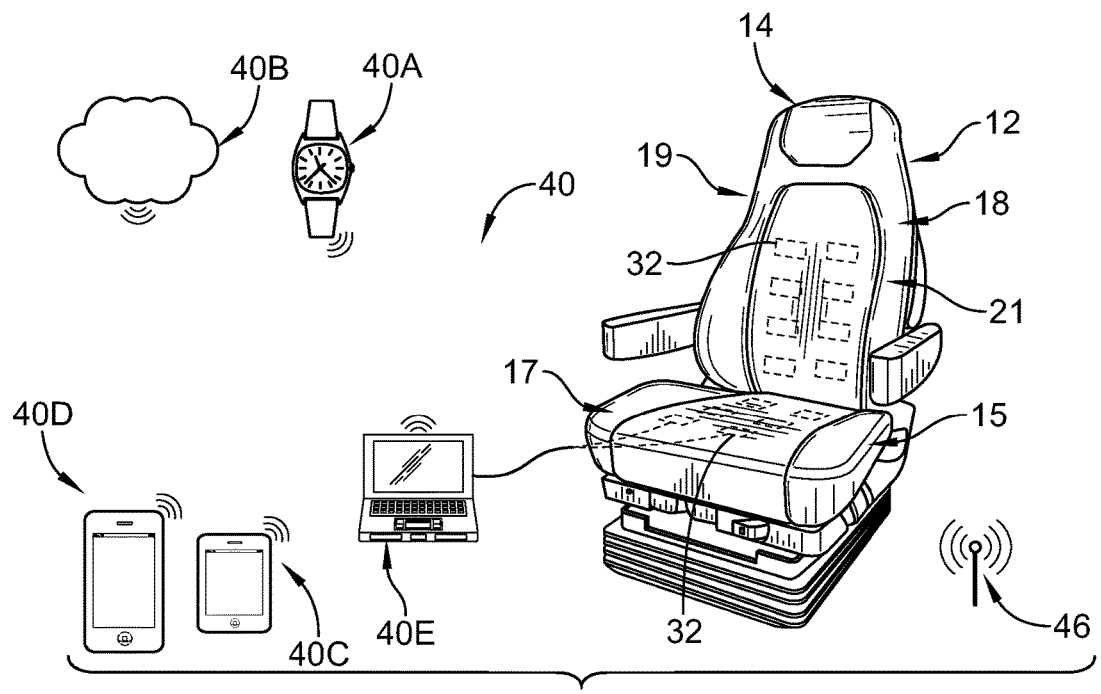
Figure 4:
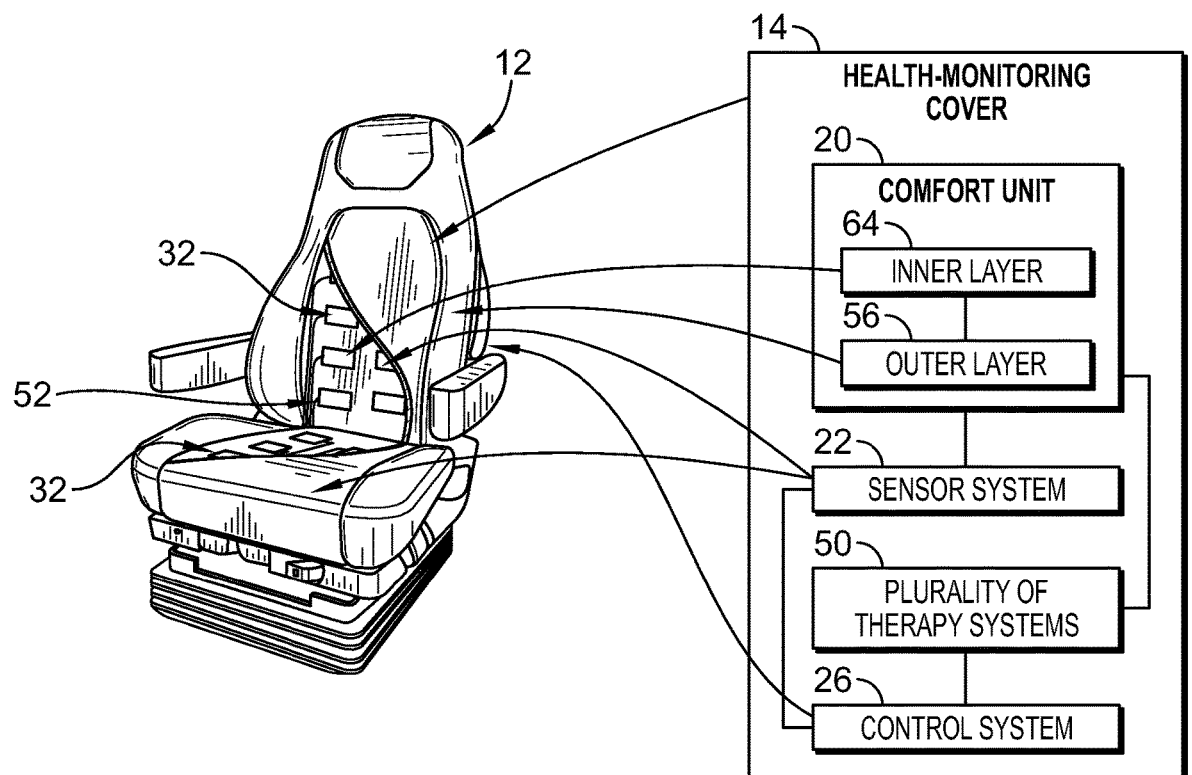
Figure 5:
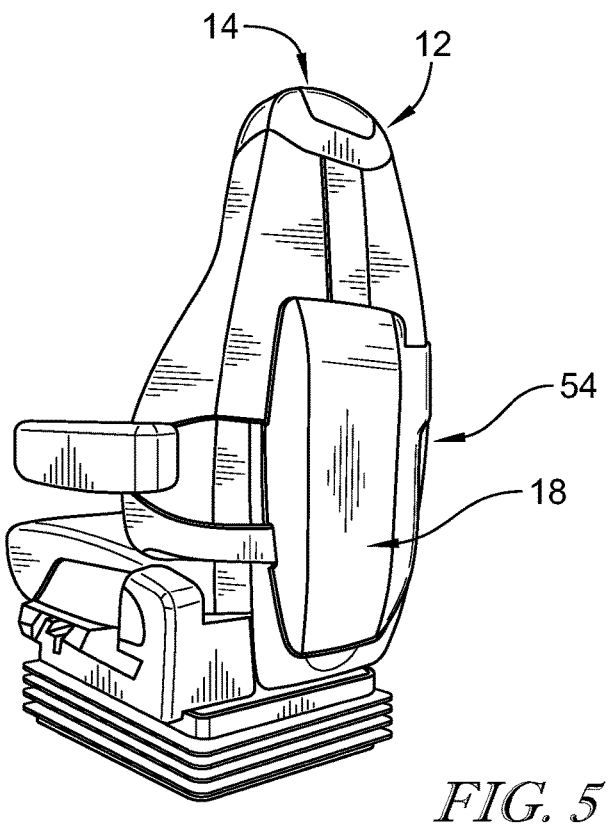
FIG. 5 is a rear perspective view of the health-monitoring cover shown in FIG. 4 showing that the health-monitoring cover includes a backpack configured to house the control system and attachment straps configured to secure the health-monitoring cover to the occupant support.

A health-monitoring cover 14 in accordance with the present disclosure is adapted for use with an occupant support 12 such as, for example, a seat as shown in FIGS. 1, 4, and 5. Occupant support 12 may be included in a vehicle or occupant support 12 may be any occupant support 12 configured to support an occupant 13. Health-monitoring cover 14 is configured to couple removably to occupant support 12 and to monitor health characteristics of occupant 13 to collect and analyze health data for informing the occupant and to generate recommendations to improve occupant's wellness and/or comfort.

Because health-monitoring cover 14 is removable, health-monitoring cover 14 may be used with multiple supports 12 and may be obtained as an aftermarket accessory separate from occupant support 12. As a result, health-monitoring cover 14 may be coupled to seats 12 for occupants with sedentary occupations such as commercial drivers or for patient data collection with healthcare providers.

Health-monitoring cover 14 may include a plurality of therapy systems 50 and may recommend activating a therapy system 50 such as a massage system 86 to improve occupant's comfort and blood flow. Over time, health-monitoring cover 14 obtains more and more occupant health data and occupant feedback to improve its recommendations and, thereby, improve occupant wellness and/or comfort.

Figure 2:
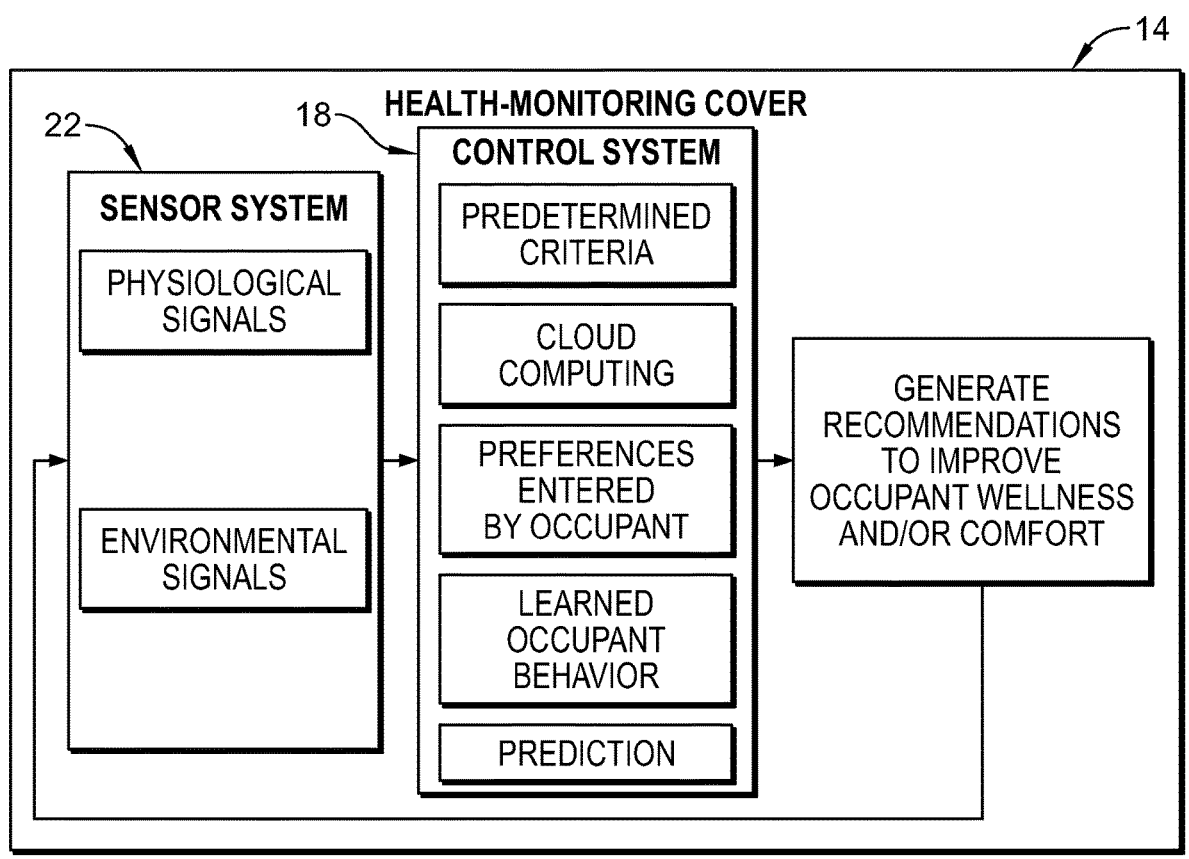

Health-monitoring cover 14 is configured to be secured removably on occupant support 12 as shown in FIG. 1. Health-monitoring cover includes a comfort unit 20, a sensor system 22, and a control system 18 as shown in FIGS. 1 and 2. Comfort unit 20 is configured to support occupant 13 on occupant support 12. Sensor system 22 is integrated with comfort unit 20 and includes a plurality of sensors 32 configured to measure occupant physiology and surrounding environment information as suggested in FIGS. 3 and 4. Control system 18 determines occupant health data indicative of physiological characteristics of occupant 13 and occupant state data indicative of a state of occupant 13 based on the signals from sensor system 22 as suggested in FIG. 11A. Control system 18 analyzes the occupant health data and occupant state data and determines recommendations for improving the wellness and/or comfort of occupant 13 as suggested in FIG. 11B.

In the illustrative embodiment, health-monitoring cover 14 further includes therapy systems 50 as shown in FIG. 4. Therapy systems 50 are connected to control system 18 and are configured to activate in response to the instructions generated by control system 18.

Illustratively, health-monitoring cover 14 is coupled removably to occupant support 12 to allow a user to move occupant support 12 from a first seat 12 to a different seat. Health-monitoring cover 14 is coupled to an outwardly facing upper surface of a driver side seat 12 as shown in FIG. 1. Health-monitoring cover 14 includes a bottom cover 17 and a back cover 19 that is coupled to and extends upwardly away from bottom cover 17. Bottom cover 17 is secured on top of a seat bottom 15 included in occupant support 12 and back cover 19 is secured on top of a seat back 21 included in occupant support 12.

Figure 6:
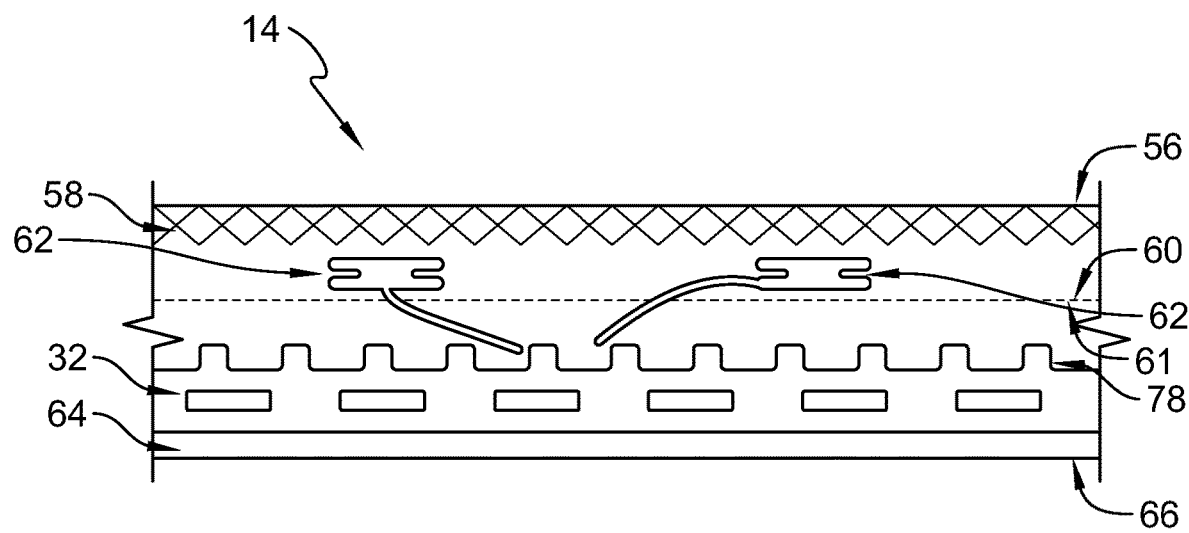
FIG. 6 is a diagrammatic cross-sectional view of the health-monitoring cover shown in FIGS. 1-5 showing that the health-monitoring cover includes an outer layer, a pneumatic bladder, a heat mat, a venting air channel layer, a plurality of sensors, and the inner layer coupled together and configured to respond to the control system.

Comfort unit 20 includes an inner layer 64 and an outer layer 56 arranged around inner layer 64 as shown in FIGS. 4 and 6. Comfort unit 20 further includes a 3D mesh layer 58 located beneath outer layer 56 as shown in FIG. 6. 3D mesh layer 58 is configured to allow for a ventilation system 88 included in therapy systems 50 to provide ventilation to occupant 13.

Comfort unit 20 may include sewn on belt attachment and toggles, nylon std clip attachments, elastic toggle tie-downs, and elastic band strap take-ups. Straps 34 may be located relatively high and low on seat back to avoid interference with side airbag deployment. Straps 34 may extend around headrest posts.

Sensor system 22 includes the plurality of sensors 32 as shown in FIGS. 3-4 and 8-9. Measurements from sensor system 22 are used to determine occupant health data and occupant state data as suggested in FIG. 3. Sensor system 22 may be included in, incorporated in, or otherwise attached to comfort unit 20. Thus, in some examples, sensor system 22 may be covered with outer layer 56 and accordingly spaced apart from occupant 13 of occupant support 12. Additionally, occupant support 12 may include a different number and/or arrangement of sensor system 22. Sensor system 22 may further be configured to provide measurements indicative of occupant behavior, vehicle conditions, and environmental conditions.

As shown in FIG. 1, sensor system 22 includes a piezoelectric sensor 28, an electrode 30, a humidity sensor 36, a thermistor 38, and smart devices 40 such as, for example, a smart watch 40A, cloud computing 40B, a smart phone 40C, a tablet 40D, a personal computer 40E and other devices with computer processors. Thermistor 38 is configured to detect occupant temperature. Smart devices 40 communicate with occupant support 12 via Bluetooth in some embodiments and may provide data in real-time when occupant 13 sits in occupant support 12. In some embodiments, sensor system 22 further includes optical cameras may include infrared cameras.

Figure 15:
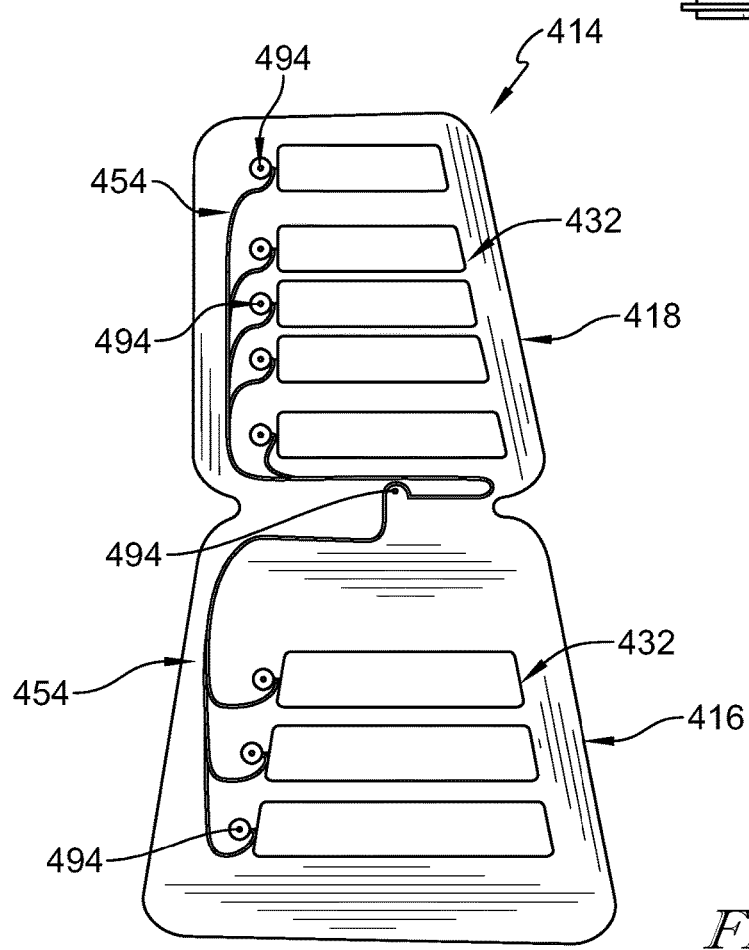
FIG. 15 is a rear perspective view of the back cover and bottom cover included in the health-monitoring cover showing the configuration of the plurality of sensors of the sensor system and showing the wires coupled to each of the sensors and secured around pins.

Sensor system 22 is configured to determine occupant health data by using the plurality of sensors 32 with the ability to be arranged in a variety of ways. The sensors 32 are configured to send information through wires 52 to control system 18. Another embodiment a health-monitoring cover 414 with a sensor system 422 is shown in FIG. 15. Sensor system 422 includes a plurality of sensors 432 spaced apart from each other with the ability to be arranged in a variety of ways. Illustratively, sensors are spaced apart from one another and located on both a bottom cover 416 and a back cover 418 as shown in FIG. 15. A wire 454 extends from each sensor and wraps around a fastener 494, such as a pin, so that wire 454 remains taught and can be lead to a bite line 12B of occupant support 12. Wire 454 is configured to couple control system 18 so that sensor system 422 is in communication with control system 18.

Control system 18 is configured to receive sensor data from sensor system 22 and determine biometric data relating to occupant 13 based on the sensor data. Thus, control system 18 is configured to measure occupant biometrics even in a noisy environment such as the interior of a vehicle when driving. Additionally, control system 18 may measure occupant biometrics with sensors 32 of sensor system 22 spaced apart from the occupant's body (e.g., to allow for seat trim and clothing), without requiring the sensors 32 to be attached to occupant 13. By measuring the occupant biometrics, control system 18 may provide biofeedback to occupant 13, trigger or suggest appropriate therapies, or perform other applications.

Figure 3:
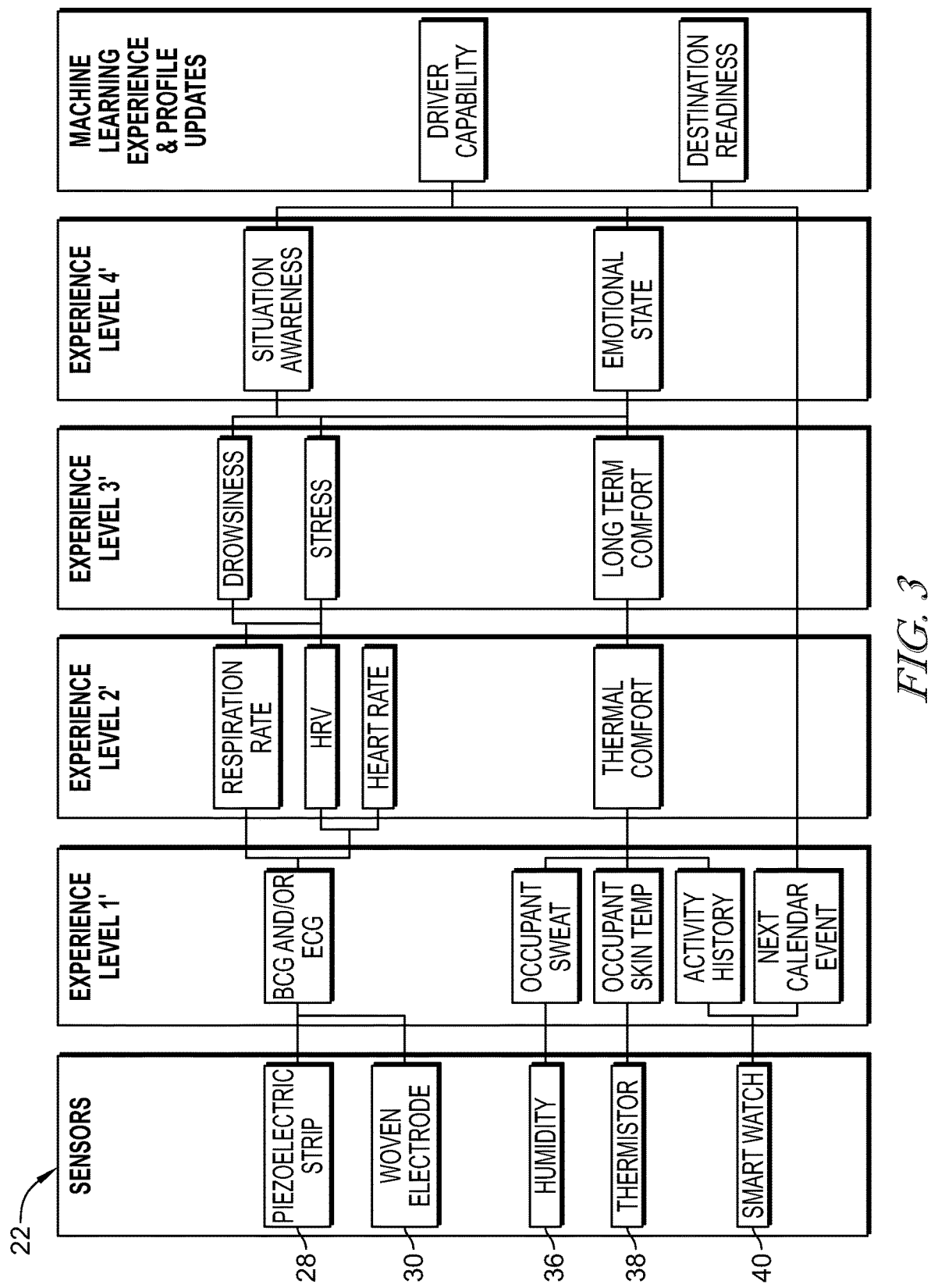
Figure 11A:
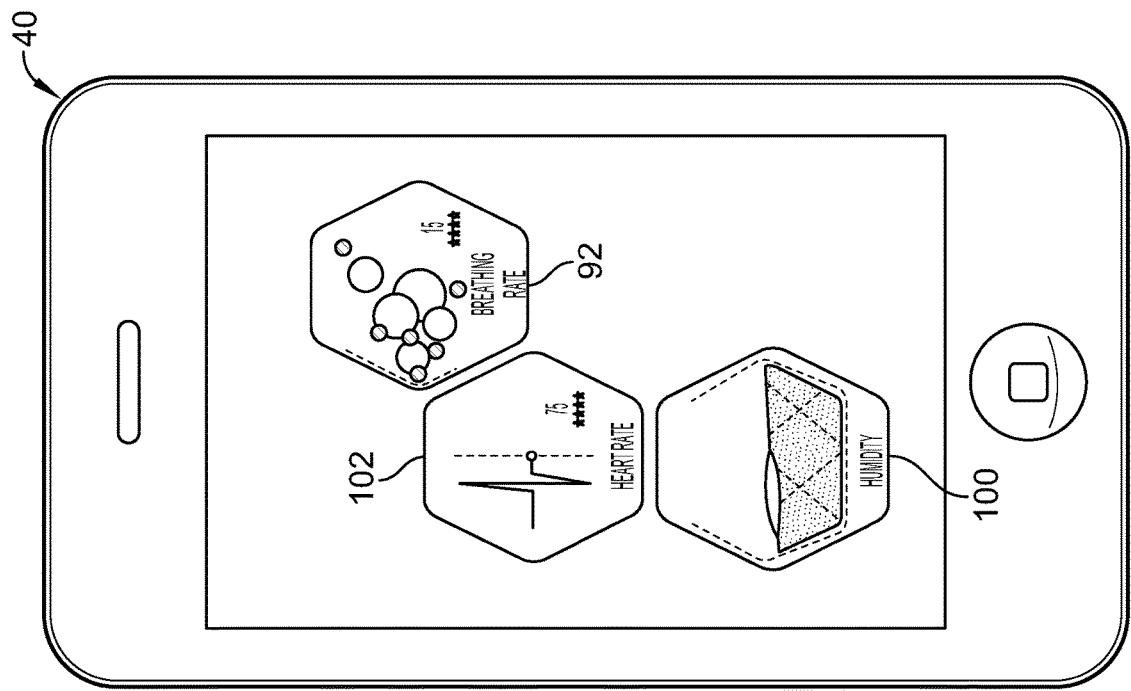
FIG. 11A is a diagrammatic view of the display screen shown on the smart device in communication with the health-monitoring cover showing occupant health data indicative of physiological characteristics of the occupant.

Control system 18 determines occupant health data and occupant state data based on the signals generated by sensor system 22 as suggested in FIGS. 3 and 11A. Control system 18 determines data based on different experience levels as shown in FIG. 3. Control system 18 is in communication with smart devices 40 in order to analyze the occupant health data and occupant state data in relation to cloud data, as shown in FIG. 1.

Cloud data includes a database, individual profiles, analyses, recommendations, and whole-life monitoring capability specific to an occupant 13 so that control system 18 is able to personalize therapy system 50 in response to the occupant's individual physiological needs and preferences. Occupant health data and occupant state data are provided in real-time to smart devices 40. FIG. 3 provides one example of the signals and data used to determine the data of experience levels 1-4 and the machine learning and profile update level. Other examples of determining data based on different signals and data are within the scope of this disclosure and a number of examples are provided herein.

As shown in FIG. 3, a plurality of biometrics and behavioral data may be collected and determined by sensor system 22 and control system 18. Reference is hereby made to U.S. application Ser. No. 15/692,396 filed Aug. 31, 2017 and titled VEHICLE SEAT for disclosure relating to sensor and therapy systems, which application is hereby incorporated in its entirety herein. Sensor system 22 and therapy systems 50/outputs of the present disclosure may include any number and combination of the sensors and output systems provided in U.S. patent application Ser. No. 15/692,396.

Control system 18 is configured to determine occupant 13 heart rate, occupant 13 sweat level, occupant 13 skin temperature, occupant 13 blood pressure, and an activity history of occupant 13 in experience level 1 as shown in FIG. 3. BCG or ECG (electrocardiogram) of occupant 13 may be determined based on signals from piezoelectric sensor 28 and electrode 30. The occupant sweat level may be based on signals from humidity sensor 36. The occupant skin temperature may be based on signals from thermistor 38. The activity history of occupant 13 may be based on signals from the smart devices 40.

Figure 18:
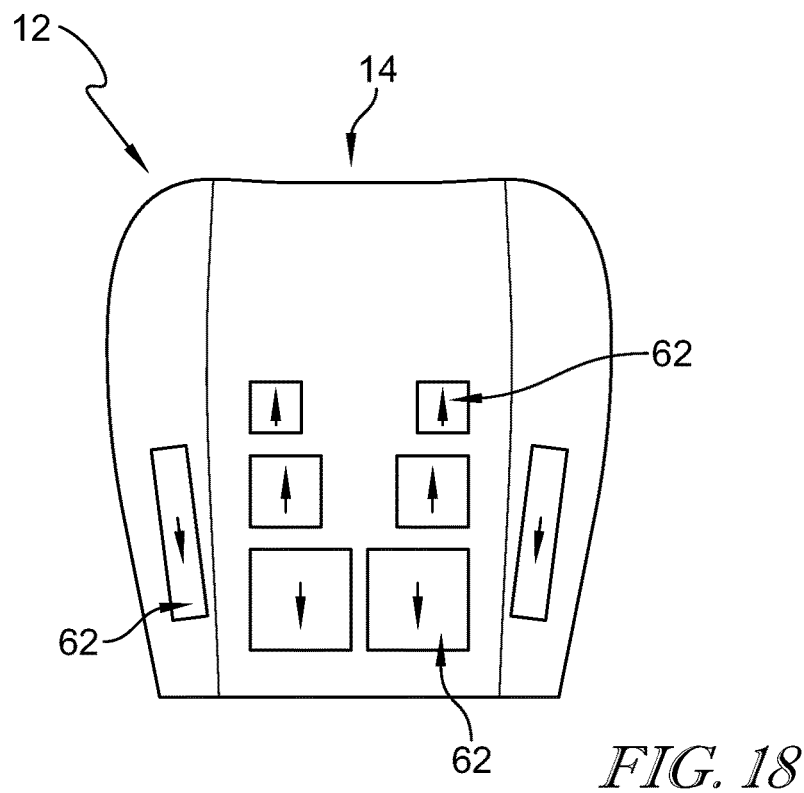
FIG. 18 is a diagrammatic view of the back cover included in the health-monitoring cover suggesting that the plurality of bladders inflate or deflate based on high or low pressure areas determined with pressure mapping, the sensors with upward facing arrows indicating an increased pressure and the sensors with downward facing arrows indicating a decreased pressure.
Figure 19:
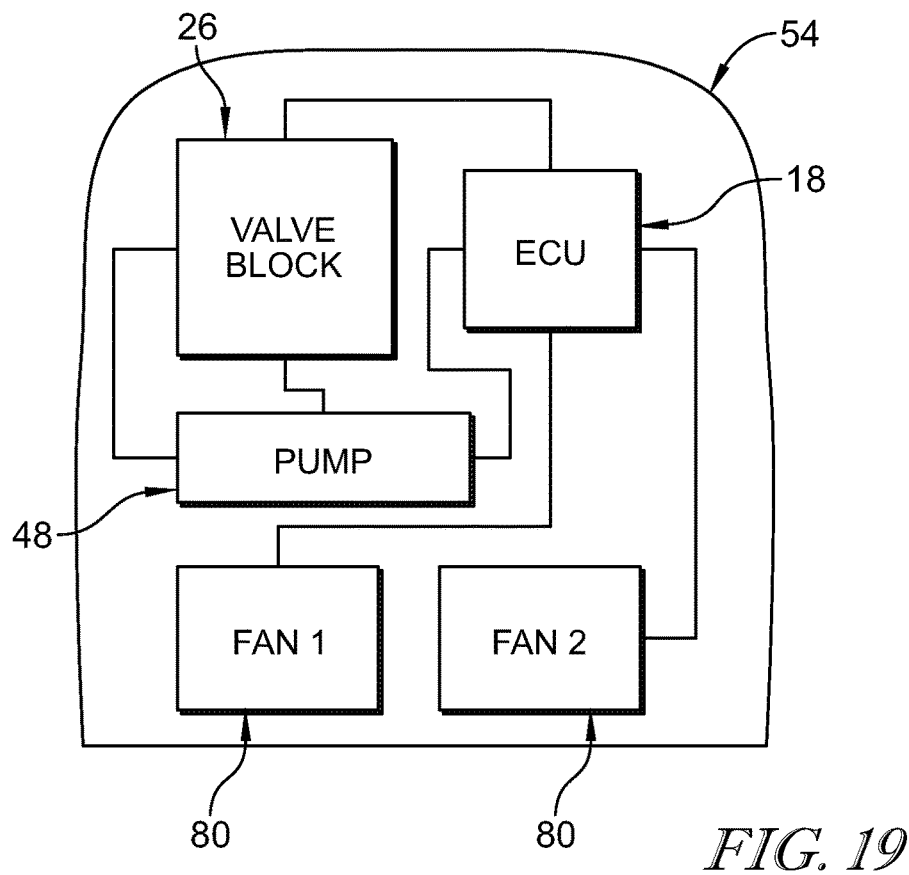
FIG. 19 is a diagrammatic view of the backpack located on the rear of the occupant support and configured to house components of the control system.

Control system 18 is further configured to pressure map the high pressure areas of an occupant's back and legs for occupant comfort and inflate pneumatic bladders 62 in response to high pressure areas as shown in FIG. 18. Sensor system 22 and control system 18 may be configured to determine a pressure map indicative of high and low pressure areas applied to health-monitoring cover 14 by occupant 13. Control system 18 is configured to adjust a pressure of the plurality of bladders based on the pressure map. FIG. 18 shows the inflating pneumatic bladders 62 with arrows pointing upward and deflating pneumatic bladders 62 with arrows pointing downward in response to control system 18 pressure mapping occupant 13. Sensors 32 may determine high pressure areas so that occupant 13 experiences improved comfort after the inflating or deflating of the pneumatic bladders 62. Therefore, even with the variability of occupant body size, pneumatic bladders 62 allow for occupant 13 to fit comfortably without altering the occupant support 12 itself.

Figure 9:
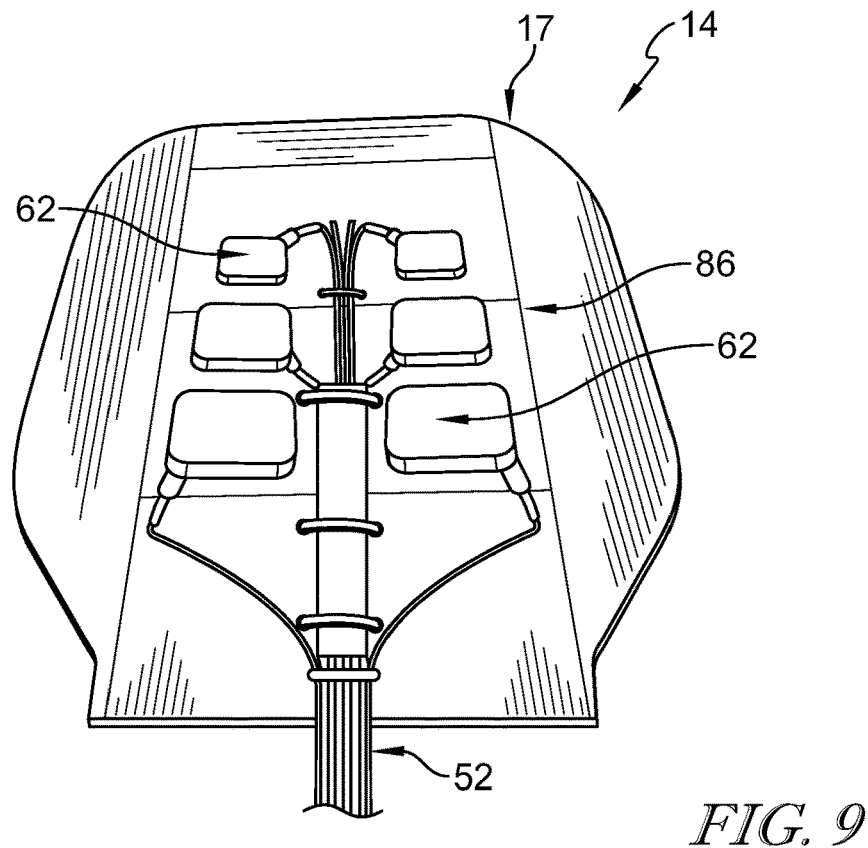
FIG. 9 is a rear perspective view of the bottom cover included in the health-monitoring cover showing the configuration of the plurality of bladders included in the health-monitoring cover.

Pressure may be determined with fluid pressure sensors, force pressure sensors, force sensors, etc. As shown in FIGS. 9 and 18, pneumatic bladders 62 near the bite line 12B may be larger than pneumatic bladders 62 located away from the bite line 12B. For example pneumatic bladders 62 may be relatively larger at a lower portion of back cover 19 and an aft portion of bottom cover 17 and pneumatic bladders 62 may be relatively smaller at an upper end of back cover 19 and a forward end of bottom cover 17. Comfort unit includes an upper end and a lower end.

The plurality of pneumatic bladders 62 includes a first pneumatic bladder located adjacent the lower end and a second pneumatic bladder spaced apart from the first pneumatic bladder toward the upper end. The first pneumatic bladder is larger than the second pneumatic bladder when both the first pneumatic bladder and the second pneumatic bladder are fully inflated. A third pneumatic bladder is located between the first and second pneumatic bladders. The third pneumatic bladder is larger than the second pneumatic bladder and smaller than the first pneumatic bladder when the bladders are fully inflated. In some embodiments, the size of the bladders is determined by volume. In some embodiments, the size of the bladders is determined by a surface area of the bladders.

In illustrative embodiments using the ACTIVE WELLNESS™ experience, as shown in FIG. 1, a learning protocol may be engaged to automate determination of the occupant status. The occupant status may be used to determine probable occupant motion sickness, stress, comfort level, apparent vigilance, and drowsiness level. The plurality of sensors provides data collection in order to determine occupant status in the learning protocol for use in the improvement protocol. The improvement protocol may comprise one or more massage programs with adjustable intensities, adjustment of seat ventilation, and adjustment of seat and/or cabin temperature.

Respiration rate of occupant 13, heart rate variation (HRV), and heart rate 102 of occupant 13 may be based on the ECG data determined in level 1 as shown in FIG. 3. The thermal comfort of occupant 13 may be based on occupant sweat level, occupant skin temperature, and activity history data determined in experience level 1. Reference is hereby made to U.S. Patent Application Publication No. 2015/0313475 filed May 18, 2015 and titled VEHICLE SEAT WITH INTEGRATED SENSORS for disclosure relating to use of sensors to obtain biometric data about an occupant, which application is hereby incorporated in its entirety herein.

Figure 11C:
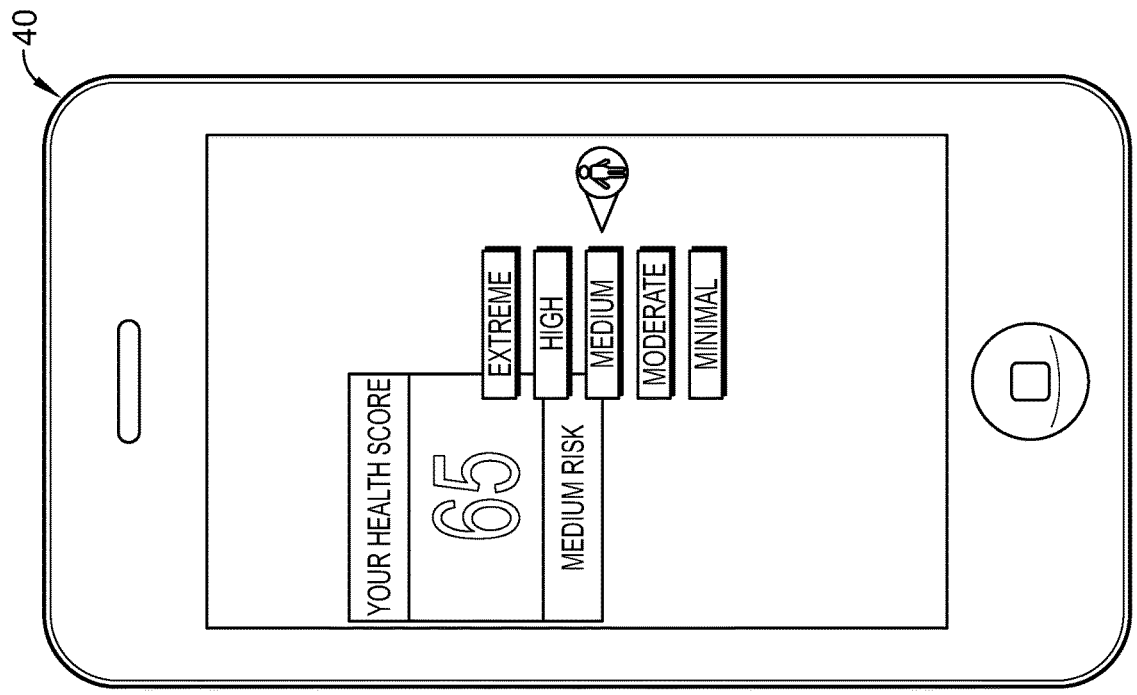
FIG. 11C is a diagrammatic view of the display screen shown on the smart device in communication with the health-monitoring cover showing that the health-monitoring cover is configured to communicate a health score of the occupant to the smart device.
Figure 11B:
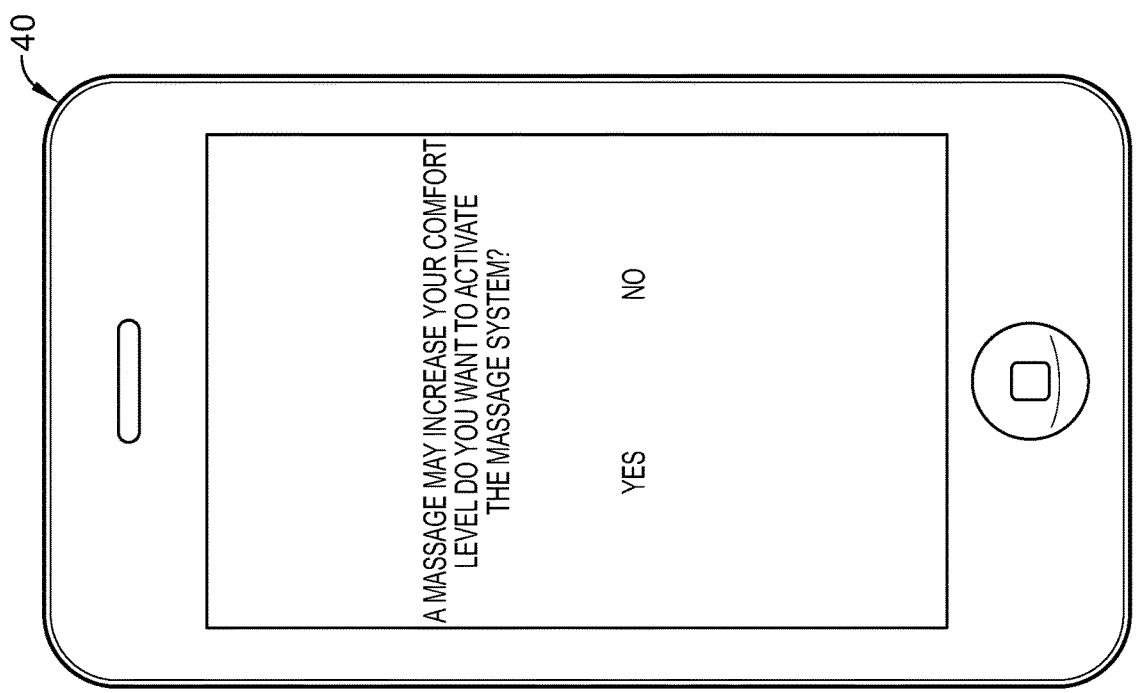
FIG. 11B is a diagrammatic view of the display screen shown on the smart device in communication with the health-monitoring cover showing that the health-monitoring cover recommends activating therapy systems to improve occupant wellness or comfort.

Control system 18 is configured to determine occupant state data based on the occupant health data and generate instructions to display the occupant health data to occupant 13 on smart devices 40 as suggested in FIGS. 1 and 11B. A plurality of states are shown and described, however other occupant states are contemplated. Occupant state data includes numerical values indicative of the severity of the state in some embodiments. In some embodiments, occupant state data is determined to be normal, low, or high based on predetermined criteria.

Drowsiness of occupant 13 and stress of occupant 13 of occupant 13 may be determined in experience level 3 as shown in FIG. 3. Drowsiness of occupant 13 may be based on one or more of respiration rate of occupant 13 and HRV of occupant 13 determined in experience levels 1 and 2. Stress of occupant 13 may be based on respiration rate and HRV data determined in experience level 2. Biometric and/or wearables including smart devices 40 include activity history with feedback from sweat and skin temperature experiences.

Fatigue minimization mode may trigger one or more different mild therapies, while the machine learns the relationship between the therapies and beneficial bio-feedback. The methods of therapy and stimulation to increase the low-fatigue zone may improve over time and may adjust to each individual's feedback. Fatigue mitigation mode may trigger more invasive therapies as well as predict and detect the onset of drowsiness. Under the high-fatigue, or impairment zone, there may be a stop mechanism available to the individual in which there is a high-risk warning. Suggestions to pull over and take a break (or other action) may be engaged.

In one example, the occupant state data may be indicative of a vigilance of occupant 13. The vigilance of occupant 13 may be based on occupant health data that includes information indicative of the respiration rate of the occupant determined from signals received from piezoelectric sensor 28 and electrode 30. In another example, vigilance may be determined based on one or more of recent activities of occupant 13 and respiration rate 94 of occupant 13.

Figure 13:
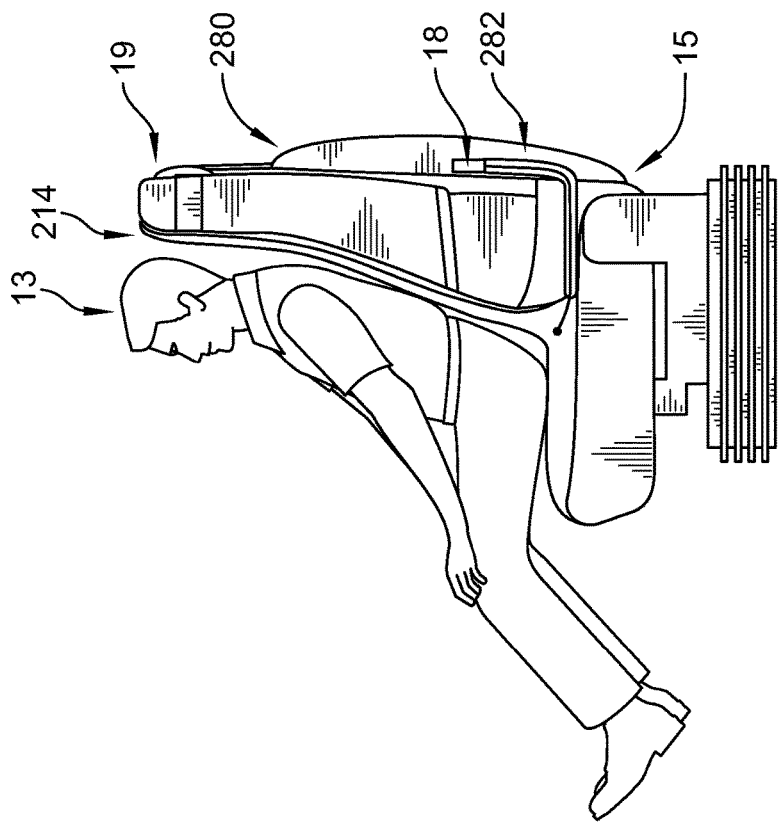
FIG. 13 is a side perspective view of a second embodiment of a health-monitoring cover coupled removeably to the occupant support showing a soft pack/pocket removeably attached a pocket on a back side of the occupant support and configured to house the control system.

In another example, the occupant state data may be indicative of motion sickness of the occupant as suggested in FIG. 13. The motion sickness may be based on occupant health data that includes information indicative of a humidity around occupant 13 determined from signals received from humidity sensor 36 and breathing rate 92 of occupant 13 determined from signals received from piezoelectric sensor 28 and electrode 30. In another example, motion sickness may be determined based on one or more of humidity around occupant 13 and breathing rate 92 of occupant 13. In yet another example, motion sickness may be determined based on humidity around occupant 13 and respiration rate of occupant 13.

In another example, occupant state data is indicative of a stress of occupant 13. The stress of occupant 13 may be based on occupant health data that includes information indicative of humidity 100 around occupant 13 determined from signals received from humidity sensor 36 and heart rate 102 of occupant 13 determined from signals received from piezoelectric sensor 28 and electrode 30. In another example, stress of occupant 13 may be based on one or more of the heart rate variability of occupant 13, humidity 100 around occupant 13, and heart rate 102 of occupant 13. In one example, stress of occupant 13 may be based on the heart rate variability of occupant 13, humidity 100 around occupant 13, and heart rate 102 of occupant 13.

In another example, occupant comfort may be based on one or more of the temperature of occupant 13, a pressure distribution of occupant 13, and the humidity 100 around occupant 13. In another example, occupant comfort may be based on the temperature of occupant 13 and humidity 100 around occupant 13.

In the illustrative embodiment, control system 18 is configured to generate instructions to display occupant health data, for example, on smart devices 40 for occupant information as suggested in FIG. 11A and configured to receive input from occupant 13 via smart devices 40. The occupant health data is displayed in geometric patterns and includes indicia of the health data and numeric values or graphical values associated with the occupant health data. Breathing rate 92, humidity 100 around occupant 13, and heart rate 102 of occupant 13 are displayed in FIG. 11A.

Control system 18 is configured to receive the occupant-body signals from sensor system 22 and determine occupant health data indicative of physiological characteristics of occupant 13 based on the occupant-body signals. Control system 18 further determines occupant state data indicative of a state of occupant 13 based on the occupant health data. Based on at least one of the occupant health data and the occupant state data, control system 18 identifies one or more of the plurality of therapy systems 50 suitable to change at least one physiological characteristic of occupant 13. For example, control system 18 may determine that a massage system 86 is suitable for changing a heart rate 102 of occupant 13. Control system 18 recommends to occupant 13 to activate therapy system(s) 50 based on the occupant health data and the occupant state data.

Therapy system 50 may be activated automatically by control system 18 or manually by occupant 13 in response to the recommendation. Alternatively, occupant 13 may activate a different therapy system 50. Control system 18 monitors which therapy system(s) 50 is activated and the effect on the occupant health data and occupant state data.

Control system 18 associates the selected therapy system 50, the occupant health data, and the occupant state data in a unique occupant data profile to learn occupant preferences and effective recommendations. Future recommendations may be based on the occupant's preferences and effective recommendations such that they are more tailored to occupant 13 over time.

Therapy systems 50 provide informational, tactile, and thermal feedback to occupant 13. Therapy systems 50, alone or in combination, may be activated to apply a variety of therapies to occupant 13 to change at least one physiological characteristic or behavioral characteristic of occupant 13. Therapy systems 50 include a temperature system 82, a massage system 86, a heat mat 60, a ventilation system 88, and smart devices 40 as suggested in FIGS. 1 and 4. Temperature system 82 includes a heating and/or cooling system included in health-monitoring cover 14. Therapy systems 50 may be activated by occupant input via smart devices 40. Therapy systems 50 may be activated automatically by control system 18.

Figure 8:
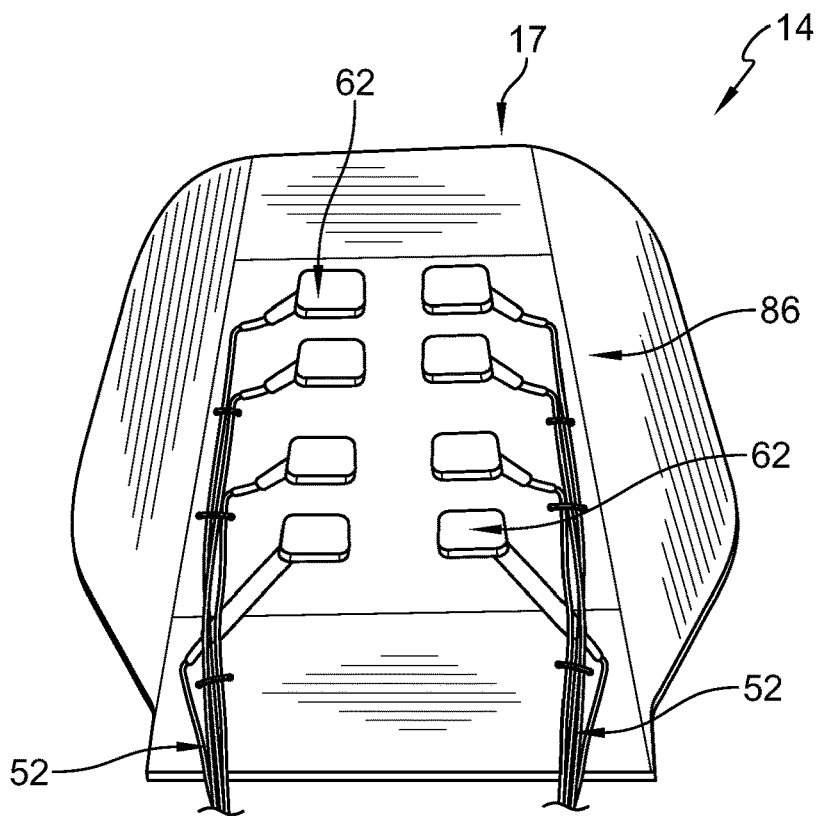
FIG. 8 is a rear perspective view of the back cover included in the health-monitoring cover showing the configuration of the plurality of bladders included in the health-monitoring cover.

The plurality of pneumatic bladders 62 are located beneath 3D mesh layer 58 as shown in FIG. 6. The plurality of pneumatic bladders 62 are configured to inflate in response to pneumatic pump 70. Illustratively, bladders 62 are spaced apart from each other and arranged so that at least eight bladders 62 are located on bottom cover 17 and at least eight bladders 62 are located on back cover 19 as shown in FIGS. 8-9.

Massage system 86 is configured to provide massage therapy to occupant 13. Heat mat 60 is located below pneumatic bladders 62 and configured to heat occupant 13 in response to thermal control system 68. Comfort unit 20 further comprises of a elastomeric venting air channel layer 78 located below heat mat 60 and configured to allow air to flow in response to activation of ventilation system 88 or other combinations of therapy systems 50, The plurality of sensors 32 are located directed beneath venting air channel 78 and inner layer 64.

With some ventilation systems, occupant weight compresses airways and blocks flow of air. Areas of the body with higher contact pressure trap heat and moisture. In the present disclosure, massaging may be performed during ventilation. When the massage system expands it provides increased ventilation. The massage sequence distributes bursts of ventilation as it progresses. In some embodiments, pneumatic bladders 62 are configured to inflate and deflate to massage occupant 13. Massaging with pneumatic bladders 62 urge occupant 13 upward and may open closed airways. As a result, massaging with pneumatic bladders 62 may be performed during ventilation to increase ventilation to occupant 13. In some embodiments, air is ventilated in bursts in response to pneumatic bladders 62 temporarily and periodically urging occupant 13 away from seat 12.

Control system 18 activates therapy system(s) 50 based on at least one of the occupant health data, the occupant state data, and input from the occupant. Activated therapy system(s) 50 may be the same or different than the recommended therapy system 50. For example, control system 18 recommends activating massage system 86, but activates temperature system 82 based on occupant input. In another example, control system 18 recommends activating massage system 86 and activates massage system 86 based on occupant input or occupant health data. Control system 18 may recommend that occupant 13 activates therapy system 50 to improve the wellness or comfort level of occupant 13 as suggested in FIG. 11B. Control system 18 may activate therapy system automatically.

Control system 18 is configured to associate activation of therapy system 50 with the occupant health data and the occupant state data in a unique occupant data profile. The unique occupant data profile is specific to one occupant and more information is added to unique occupant data profile over time to increase the accuracy and effectiveness of the recommendations made by control system 18. Control system 18 is configured to identify occupant 13 based on at least one of input from occupant 13 and the occupant health data.

Data associated in unique occupant data profile includes occupant height, weight, sex, and age data. Such data may be entered manually by occupant 13, by smart devices 40, and/or by an Internet connection. Unique occupant data profile further includes a medical history including medical conditions of occupant 13. A completion level of the unique occupant data profile may be depicted by shading of silhouette from foot to head. No shading corresponds to an incomplete profile and full shading corresponds to a complete profile.

By associating associate activation of therapy system 50 with the occupant health data and the occupant state data in the unique occupant data profile, control system 18 learns occupant preferences and behaviors over time. If the recommended therapy system 50 is activated, control system 18 learns that occupant 13 agrees with that recommendation while occupant 13 exhibits that occupant health data and occupant state data. If the recommended therapy system 50 is not activated and instead, another therapy system 50 is activated, control system 18 learns that occupant 13 prefers the other therapy system 50 while occupant 13 exhibits that occupant health data and occupant state data. Control system 18 learns and improves its recommendations as the number of iterations increase.

Control system 18 is configured to determine the effectiveness of activating therapy system 50. Control system 18 monitors and analyzes the physiological data of occupant 13 to determine the effect of therapy systems 50 on occupant 13. In one example, control system 18 is configured to receive supplemental occupant-body signals and supplemental behavioral signals after activating the therapy system 50. Control system 18 determines supplemental occupant health data based on the supplemental occupant-body signals. Control system 18 determines supplemental occupant state data based on the supplemental occupant health data.

Control system 18 identifies therapy system(s) 50 configured to change at least one physiological characteristic of occupant 13 based on at least one of the supplemental occupant health data, the supplemental occupant state data, and the unique occupant data profile. Control system 18 activates therapy system(s) 50 based on at least one of the supplemental occupant health data, the supplemental occupant state data, the unique occupant data profile, and input from occupant 13. The activated therapy system 50 may be the same or different than the previously activated or recommended therapy system 50.

Control system 18 is configured to associate activation of therapy system(s) 50 with the supplemental occupant health data and the supplemental occupant state data in the unique occupant data profile to learn occupant behavior and preferences. Control system 18 compares the occupant health data and the supplemental occupant health data and associates changes to the occupant health data in the unique occupant data profile.

Control system 18 may further include a digital signal processor, GPS-Fit, Bluetooth to a mobile device, and a wired or wireless connection to a vehicle on-board diagnostics. Control system 18 may also include a thermal control system 68 configured to communicate with heat mat 60 as well as controlling pumps, massage, bolsters, GPS-Fit and valve blocks 26.

Control system 18 determines a health score of occupant 13 in some embodiments, as suggested in FIG. 11C. Control system 18 is configured to receive secondary health data unique to occupant 13 from at least one of an input and an accessory device. For example, secondary health data includes a height, sex, weight, and/or age of occupant 13. Secondary health data may include a medical history and medical conditions of occupant 13 input manually or received via a smart device or over an internet connection. Control system 18 associates the secondary data with the unique occupant data profile and determine the health score of occupant 13. Control system 18 generates instructions to display the health score to occupant 13 as suggested in FIG. 11C.

In one example, the health score is based on the occupant health data, the unique occupant data profile, and predetermined criteria. In another example, the health score is based on the occupant health data, the unique occupant data profile, the secondary health data, and predetermined criteria. In some embodiments, the health score is based on cloud data of other vehicle occupants.

In some embodiments, control system 18 analyzes the occupant data over a period of time and provides a raw health score. The raw scores are tallied and compared to predetermined criteria. The raw scores are normalized for the occupant's particular occupant profile and history. Control system 18 generates instructions for outputting the health score.

In some embodiments, control system 18 anticipates occupant's 13 use of occupant support 12 amenities and therapies such as, for example, therapy systems 50. Occupant 13 is connected with occupant support 12 via smart devices 40.

In one scenario, occupant support 12 detects that occupant 13 has is experiencing a heightened heart rate. Occupant support 12 suggests comfort rejuvenation, which may include a massage and activation of ventilation based on sensor measurements. In another scenario, occupant support 12 prepares occupant 13 for physical activity by giving a stretching massage.

In another example, fatigue of an occupant 13 may be detected and predicted based on a number of factors. An occupant-driver fatigue curve may be projected to occupant 13 and may help schedule a trip to minimize fatigue before the trip starts. Control system 18 may inform or suggest to the driver when and where to take a break from driving, as well as provide reminders for a break during the trip. Occupant may 13 provide inputs and at least portions of the operator profile to the system. Preference modifications may be provided by the system and considered in planning for restorative sleep in a multi-day journey.

Each occupant health data type is rated as normal, high, or low in some embodiments. If one or more of the occupant health data used to determine an occupant state is not normal, control system 18 determines one or more therapy system 50 to recommend to occupant 13 in order to change the occupant health data toward normal. Occupant health data and occupant state data is continually monitored and recommendations are provided until occupant health data and occupant state data are normal. Occupant medical history and conditions are taken into account in determining normal occupant health data and occupant state data.

Figure 12:
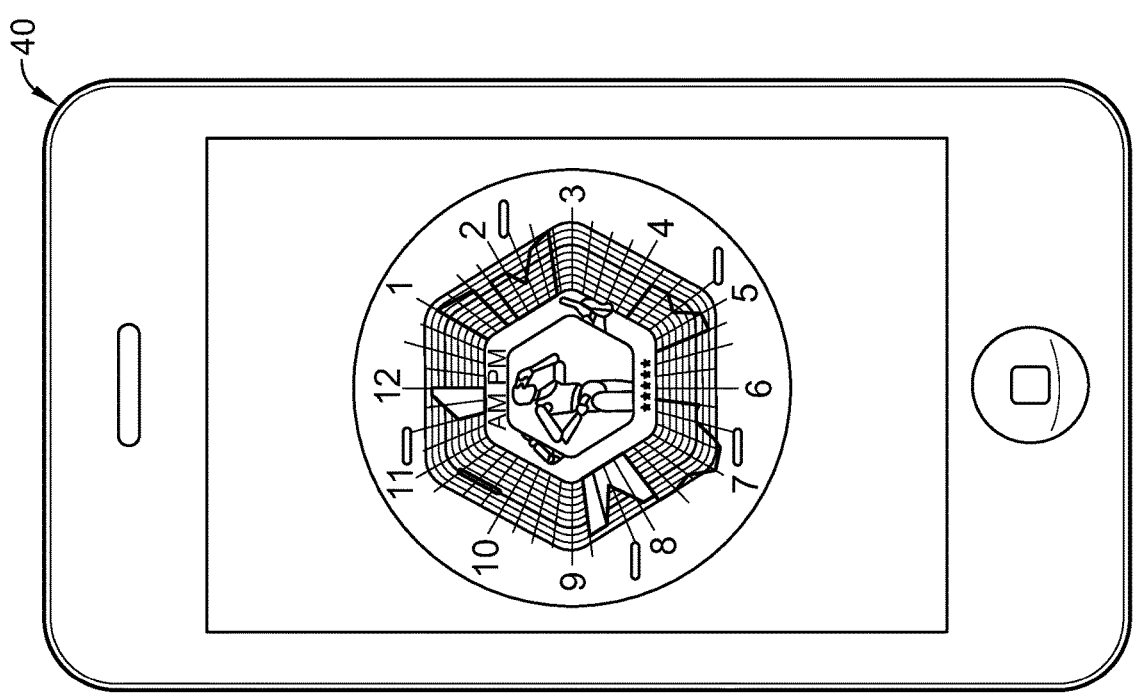
FIG. 12 is a diagrammatic view of display screen shown on the smart device in communication with the health-monitoring cover showing occupant data over time.

Control system 18 is configured to connect to one or more of smart devices 40 and communicate with occupant 13 via the smart device such as via a display screen. As such, health-monitoring cover 14 may interact with occupant 13 and provide the determined data and recommendations to occupant 13 through a plurality of the occupant's smart devices. Health-monitoring cover 14 may receive occupant input via smart devices 40. In other embodiments, control system 18 includes a display and/or audio output. Control system 18 is configured to generate instructions to display occupant health data and/or occupant state data in a graphical representation as shown in FIG. 12. The occupant health data and/or occupant state data is graphed over a 12-hour period in the illustrative embodiment.

Figure 7:
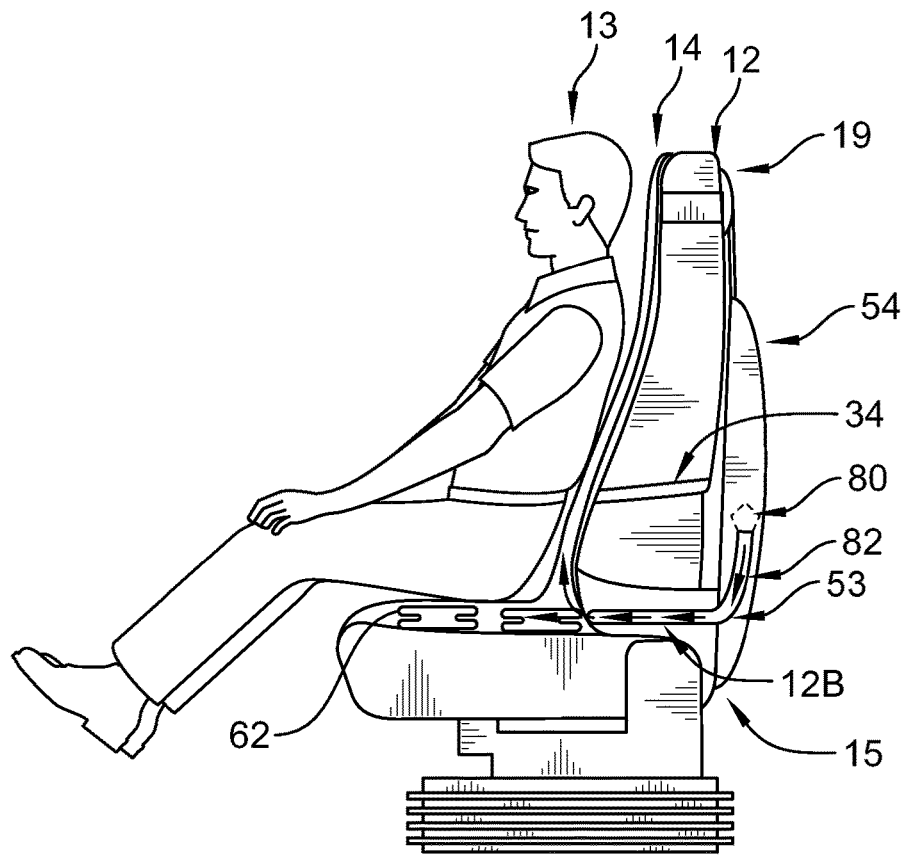
FIG. 7 is a side perspective view of the health-monitoring cover showing the backpack removeably attached to the occupant support and configured to house the control system and a fan, the fan configured to direct air into the comfort unit so that the occupant experiences a cooling sensation in response to the activation of the fan.

Illustratively, control system 18 is located in backpack 54 coupled to a back of occupant support 12 as shown in FIGS. 1, 3, 4. Backpack 54 may be connected to health-monitoring cover 14 through wires 52 extending through the vehicle seat bite or bite line so to communicate the desired therapy to occupant 13. Air flow may be provided from backpack 54 to occupant 13 as shown in FIG. 7. The airflow is illustrated with arrows and shows the flow moving downward from the top of the seat back of the vehicle seat to the bottom of the seat back of the vehicle seat. The air flow continues to flow through the seat bite or bite line while splitting the airflow in two directions across the occupant side of the vehicle seat 12. A portion of the airflow goes upward on the occupant side of the vehicle seat back while a portion of the flow travels along the occupant side of the seat bottom of the vehicle seat as shown in FIG. 7. Illustratively, backpack 54 is created using Cover Carving Technology (CCT) which provides for a form-fitting backpack 54 and additional knee room for rear passengers and allows for a semi-rigid, resistant, and lightweight backpack 54. CCT may involve less tooling costs and allows for backpack 54 to be coupled to the seat cover 14 with no fixation to the occupant support 12.

Figure 14:
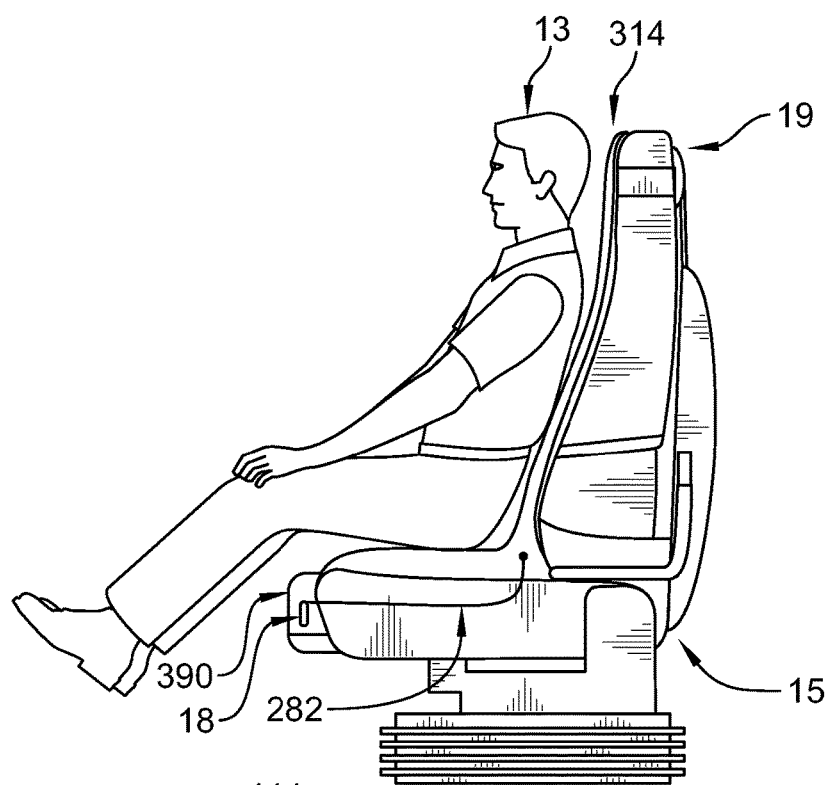
FIG. 14 is a side perspective view of a third embodiment of a health-monitoring cover coupled removeably to the occupant support showing a front pocket attached removeably to the occupant support and configured to house the control system.

In another embodiment of health-monitoring cover 214, control system 18 and the aforementioned electronic equipment associated with the health-monitoring cover may be located in a soft pack/pocket 280 coupled to the back of vehicle seat 12 as shown in FIG. 13. In additional embodiments, control system 18 and the aforementioned electronic equipment associated with the health-monitoring cover 314 may be located in a front pocket 390 coupled to the front edge of the seat bottom of the vehicle seat 12 as shown in FIG. 14.

Figure 16A:
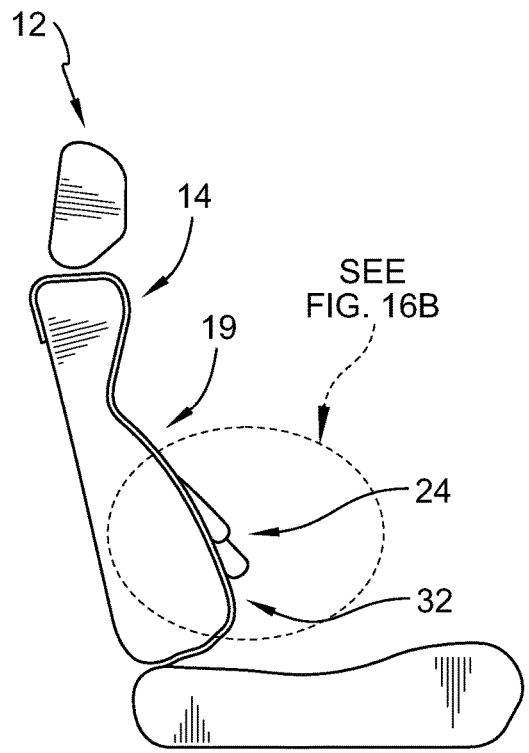
FIG. 16A is a side perspective diagrammatic view of the health-monitoring cover showing that the health-monitoring cover includes a plurality of adjustable lumbar bladders to provide lumber support separate from the occupant support.
Figure 16B:
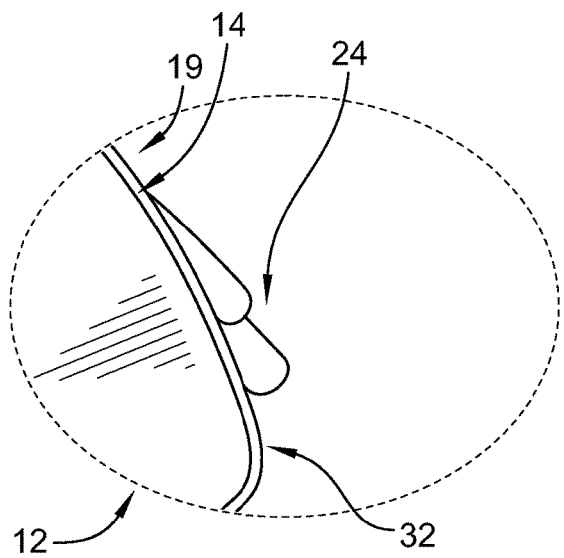
FIG. 16B is an enlarged diagrammatic view of the health-monitoring cover shown in FIG. 16A.
Figure 20:
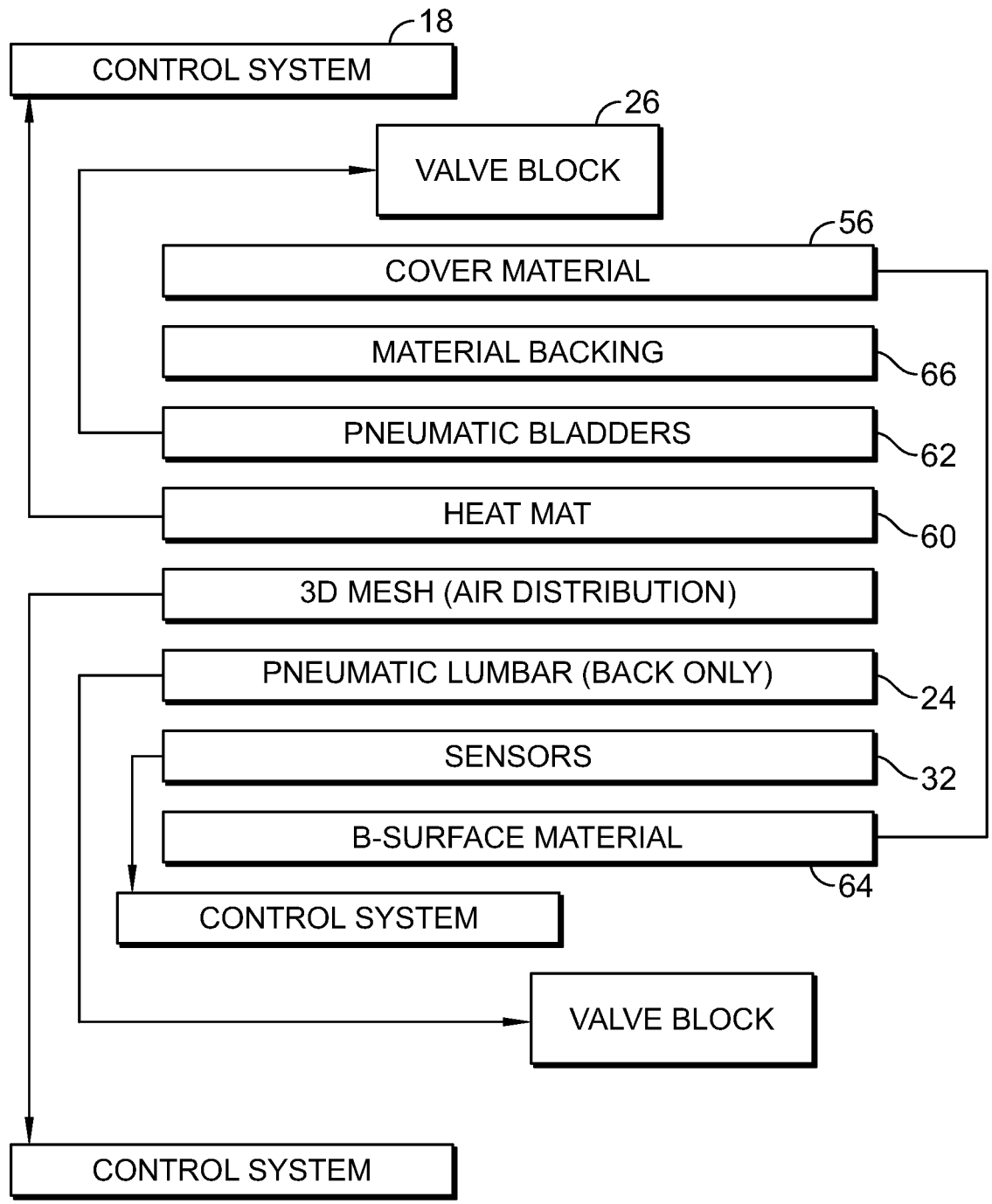
FIG. 20 is a diagrammatic view of the health-monitoring cover showing the components of the health-monitoring cover and the connections made at each layer.

Illustratively, health-monitoring cover 14 further includes pneumatic lumbar bladders 24 located between sensor system 22 and 3D mesh layer 58 as shown in FIGS. 16 and 20. As such, health-monitoring cover 14 provides adjustable lumbar support for occupant supports that may not include adjustable lumber support. Lumbar bladders 24 are arranged so that when occupant 13 sits on occupant support 12, he/she experiences support in his/her lumbar region of his/her low back. Lumbar bladders 24 may inflate or deflate in response to a valve block 26 located in control system 18. Lumbar bladders 24 are in communication with valve block 26 so that they are configured to inflate or deflate via pump 48 and fans 80. Illustratively, lumbar bladders 24 are inflated simultaneously in order to create lumbar support. Lumbar bladders 24 inflate and deflate relative to each other so that lumbar bladders 24 can be adjusted four ways (up, down, inward, and outward).

Figure 17A:
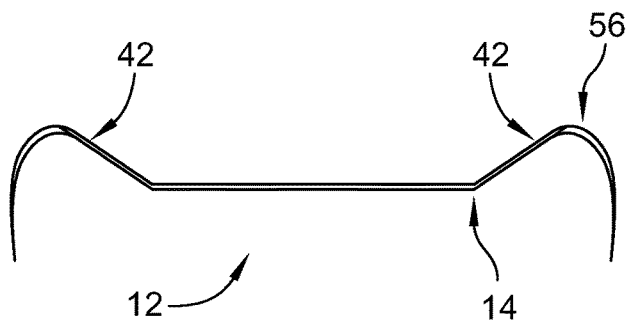
FIG. 17A is a top perspective view of the health-monitoring cover showing that the health-monitoring cover includes a plurality of adjustable bolsters for providing support separate from the occupant support, the bolsters being currently deflated.
Figure 17B:
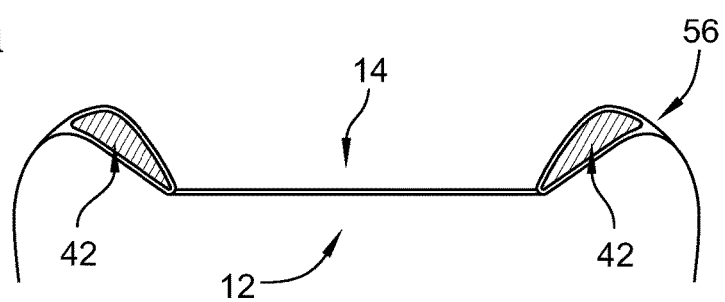
FIG. 17B is a top perspective view of the health-monitoring cover showing the plurality of bolsters have been inflated.

Illustratively, health-monitoring cover 14 further includes adjustable bolsters 42 located between outer layer 56 and inner layer 64 of back cover 19 of health-monitoring cover 14 so that the head of the occupant is flanked by adjustable bolsters 42 as shown in FIGS. 17A and 17B. The adjustable bolsters 42 are configured to be inflated or deflated in order to increase the support of an occupant's head. Comfort unit includes a first lateral side and a second lateral side spaced apart from the first lateral side. Adjustable pneumatic bolster bladders 42 include a first pneumatic bolster bladder located adjacent the first lateral side and a second pneumatic bolster bladder spaced apart from the first pneumatic bolster bladder and located on the second lateral side of the comfort unit.

In an illustrative embodiment, the health-monitoring cover 14 includes outer layer 56 (sometimes called a cover material) and a material backing 66 as shown in FIG. 20. Material backing 66 is located between outer layer 56 and pneumatic bladders 62, pneumatic bladders 62 being in communication with valve block 26. Pneumatic bladders 62 are arranged on top of heat mat 60, and heat mat 60 is in communication with control system 18. Heat mat 60 is located on top of a layer of 3D mesh 58 so that therapies 50 may be experienced by occupant 13. 3D mesh 58 may be in fluid communication with control system 18 and some therapy systems 50 such as ventilation system. Pneumatic lumbar bladders 24 are located underneath 3D mesh 58 and above sensors 32 and are in communication with valve block 26 and are only located in the back cover 19 of the health-monitoring cover 14. Sensors 32 are in communication with control system 18 and are arranged on top of the inner layer 64. Inner layer 64 may also be called backing material 64 and B-surface material 64. Any number of components in cover 14 may be omitted in some embodiments. In other embodiments, components in cover 14 are rearranged.

A method of using health-monitoring cover 14 may include a number of steps. The method may include providing a health-monitoring cover configured to couple removably to an occupant support, the health-monitoring cover including a comfort unit configured to support an occupant of the occupant support, a sensor system, and a control system. The method may further include measuring, with the sensor system, occupant-body signals associated with physiological characteristics of the occupant. The method may further include determining, with the control system, occupant health data indicative of physiological characteristics of the occupant based on the occupant-body signals. The method may further include transmitting, with the control system, the occupant health data to a smart device.

The method may further include generating instructions to activate one of the massage system, ventilation system, and heating system based on the occupant health data. The method may further include conducting air flow with the ventilation system through a bite line defined by a seat bottom and a seat back of the occupant support.

The method may further include generating instructions to display the occupant health data on a screen with the control system. The method may further include measuring a pressure of the plurality of pneumatic bladders with the sensor system. The method may further include generating instructions to adjust the pressure in the plurality of pneumatic bladders with the control system. The method may further include adjusting a pressure in the pneumatic lumbar bladder with the control system based on the occupant health data. The method may further include adjusting a pressure in the pneumatic bolster bladder with the control system based on the occupant health data.

According to the present disclosure, an occupant wellness sensor pad system (sometimes called a health-monitoring cover) is provided for installation in original-equipment seats or as an aftermarket product. The occupant wellness system may include a seat mat with back and bottom portions. It may also include a sensor array, electronic control system, at least one integrated therapy system, and capability for connection to cloud data using a wireless connection means and electronic device. The occupant wellness sensor system pad system may be installed on a vehicle seat at the seat bottom, seat back, or at a combination thereof. A map pocket may be used to house electronic equipment associated with the system. Alternatively, a seat bottom front pocket may be used to house the electronic equipment.

In illustrative embodiments, integrated therapies into the occupant wellness sensor pad system may include a massage therapy system, thermal therapy system, or a combination thereof. A sensor array may be included in the system to detect and measure biometrics of an occupant of a vehicle seat. The massage therapy system may include pneumatic bladders. The thermal therapy system may include a heat mat. Each of the therapies may require a different internal pad structure, for example differently-shaped or oriented layers, to reliably deliver such therapies.

The occupant wellness sensor pad system provides a user with an aftermarket experience of an Active Wellness® closed-loop biometric measurement and therapy system. The system may be used by long-haul truck drivers, agricultural machine operators, bus drivers, taxi drivers, pilots, or anyone spending significant amounts of time in a vehicle. General health monitoring such as heart rate, respiration rate, blood pressure, etc. may be addressed. Therapies such as heating or venting, massage, breathing exercises, music, and situational awareness (via GPS-Fit) may also be addressed.

Features that may be integrated or connected to the system include Smart-Fit, GPS-Fit, personal wearable devices, and other biometric monitoring and health technologies. Breathing pattern and level, exercises and intensities, prompting for activity, step-tracking, and sleep-tracking may be monitored for a whole-life activity profile. The option for tracking fatigue due to under-stimulation or drowsiness (e.g. due to circadian rhythm) may also be provided in a new form factor in the present disclosure.

Health-monitoring cover 14 may include a sensor system 22 operatively connected to an electronic control system 18 to provide instructions on engaging a therapy system 50 in a vehicle seat 12. The electronic control system 18 may communicate with a smart device 40 for analyzing the individual occupant data in relation to cloud data, as suggested in FIG. 1.

Cloud data may include a database, individual profiles, analyses, recommendations, and whole-life monitoring capability. Wireless connection means 22 may be used to connect the mobile device with the electronic control system, including but not limited to Wi-Fi 46 and Bluetooth capability. Modes of physiological improvement may include the occupant simply building awareness and tracking habits of physical characteristics that are monitored by the occupant wellness sensor pad system 14. Biofeedback, psychosomatic, and induced physiological response to therapies are also introduced in the present invention. Electronic monitoring of a normally-automatic bodily function (e.g. breathing rate) may be used to train someone to acquire voluntary control of such a function, for example. Likewise, a person that becomes aware of an unfavorable habit (e.g. driving when drowsy) may be likely to expend effort to overcome the unfavorable habit when notified of it by the sensor system.

The electronics equipment may be stored in a location free from interference with the occupant's use of the vehicle cabin. One solution provided is to include the equipment in a soft pack/pocket 280 located at the rear portion of a vehicle seat 12 back with respect to the location of the occupant as shown in FIG. 13. Any number of wires or harnesses 282 may be routed through the seat bite or bite line of the vehicle seat 12. Another option may be to provide the wiring or harness 282 route through the seat bottom to be stored in the seat bottom front pocket 390 as shown in FIG. 14. Yet another option may include a seatback equipment backpack 54 as shown in FIGS. 4 and 7.

The seatback equipment backpack 54 may be connected to a seat cover through the vehicle seat bite or bite line. The electronic control system 18 may include a digital signal processor (DSP), GPS-Fit, Bluetooth to a smart device 40, and a wired or wireless connection to vehicle on-board diagnostics (OBD). A thermal control system 68 may be integrated or included as a separate component for an integrated heat mat 60.

Pneumatic functionality may also be included for controlling pumps, massage, bolsters, GPS-Fit, and valve blocks 26. Air flow may be provided from the back of the seat back with respect to the location of the occupant 13 as shown in FIG. 7. The airflow is illustrated with arrows and shows the flow moving downward from the top of the seat back to the bottom of the seat back, continuing to flow through the seat bite or bite line while splitting the flow in two directions across the occupant side of the vehicle seat 12. A portion of the flow may go upward on the occupant side of the seat back 6 while a portion of the flow travels along the occupant side of the seat bottom as shown in FIG. 7. Control system 18 may be configured to activate functional pneumatics of the health-monitoring cover 14. The seat bite or bite line may be blocked by a toe kick in some vehicles, in which packaging may be slightly modified to fit the packaging space provided by that particular space between the seat bottom and the seat back.

Figure 10:
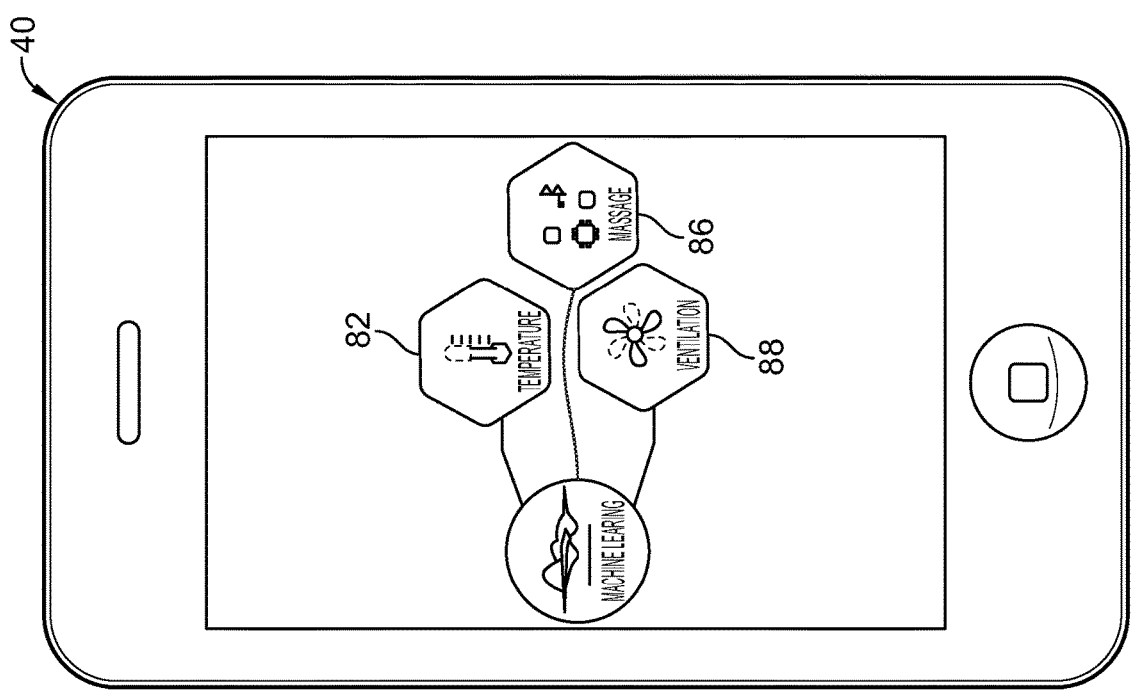
FIG. 10 is a diagrammatic view of a display screen included in a smart device suggesting that the smart device is in communication with the health-monitoring cover and configured to display information about the therapy systems included in the health-monitoring cover such as a temperature system, a ventilation system, and a massage system.

One embodiment may include sensors only with the binding trim edge made of a laminated cover material. A non-skid closeout material may be used with a sensor array and separately-fabricated seat cushion portion and seat back portion. The portions may be sewn together. Nylon standard clips or other attachment mechanism may be sewn on the belt attachment and toggles with an elastic tie-down and elastic band strap take-up. The seat coverlet may include all of the above-referenced components and the therapy components may be external to the coverlet. The belt arrangement will be set up to avoid covering the side airbag at the seat back. An indicia or logo may be included as part of the health-monitoring Adhesive may be used to secure any wire or harness as shown in FIGS. 8 and 9. Strain relief is provided by wrapping the paired wires 454 around a pin or other stabilizing post 494 as shown in FIG. 15. Excess tape or a second piece of tape may be used to close the wire harness. Sensor strips of the sensor system 22 on seat back are shown in FIG. 15. Sensor strips of sensor system 22 on seat bottom are shown in FIG. 10B. An unshielded wire harness includes a predetermined length of sensor wire that has individual grounds for each of the paired wires 454.

The seat bottom portion of the occupant wellness sensor pad system 14 is shown in FIGS. 12A and 12B. The occupant side of the pad cover has a plush or other desired textile finish. The back is preferably coated or made of a non-slip material and the wire harness exits at the center portion of the seat bottom of sensor pad system 14.

Health-monitoring cover 14 may include multiple connections to the sensor array within the cover. The electronic control system 18 may include standard or custom connectors that meet predetermined specifications based on the application of the health-monitoring cover 14. Illustratively, harnesses and their corresponding connectors may be used.

Massage therapy system 86 may include bladders on both the seat back and seat bottom. Health-monitoring cover 14 includes pneumatic bladders 62 on the rear of the seat back. A sensory array may be located on the front of the seat back. The electrical connection at the center of the seat back. The cover of the seat back on the occupant side when the sensors are covered. The order of orientation of the massage components, sensor array, and heating mat may be adjusted to fit any particular seat's bite line. The massage therapy system 86 may include pneumatic bladders 62 on the seat bottom.

The layers of health-monitoring cover 14 may include a cover with three-dimensional mesh material, pneumatic bladders, a heat mat 60 with air flow openings 61, an elastomeric (or other suitable material) venting air channel layer, a sensor layer, and a back material. FIG. 7 illustrates a cross-section of an occupant seated in a vehicle seat 12 while the pneumatics are engaged to provide airflow, as shown by arrows. Cover layer may be on the occupant side of the vehicle seat, with heat mat 60, venting air channel 78, plurality of sensors 32, and material backing 66 to follow. The air channels in the elastomeric layer may provide for unobstructed passage of air. The three-dimensional mesh sewn to the outer layer 56 may provide a plush surface for the occupant while allowing the passage of air.

An alternative construction may include a fan 80 to provide forced ventilation in backpack 54 with ducting 53 or wiring 52 passing through the seat bite 12B or bite line. The airflow may then split after the seat bite or bite line to the seat back and seat bottom as shown in FIG. 7. An equipment backpack 54 may be made of any suitable material.

In one embodiment, an occupant wellness sensor pad system connected to a vehicle seat includes a seat mat with a seat back portion and seat bottom portion, a sensor array, an electronic control system, at least one integrated therapy system, and a wireless connection means through an electronic device. The occupant wellness pad system is installed on a vehicle seat at the seat bottom, seat back, or at a combination thereof, electronics may be housed within at least a portion of the vehicle seat.

The occupant wellness pad system may include integrated therapy means comprising optionally one or more of a massage therapy system and a thermal therapy system. The occupant wellness pad system may include a sensor array to detect and measure biometrics of an occupant seated in the vehicle seat. The occupant wellness pad may include pneumatic bladders. The occupant wellness pad may include a heat mat. The occupant wellness pad system may include a closed-loop biometric measurement and therapy system, with detection and determination of heart rate, respiration rate, and blood pressure. The occupant wellness sensor pad system may include a closed-loop biometric measurement and therapy system, with detection and determination of occupant presence.

The invention claimed is:

1. A health-monitoring cover adapted for use with an occupant support, the health-monitoring cover comprising
   a comfort unit configured to couple removably to the occupant support adapted for use in a vehicle, the comfort unit including an inner layer and an outer layer arranged around the inner layer,
   a sensor system integrated with the comfort unit, the sensor system configured to obtain occupant-body signals associated with physiological characteristics of an occupant of the occupant support, a plurality of therapy systems integrated into the comfort unit and configured to relieve the occupant, a control system configured to receive the occupant-body signals from the sensor system, determine occupant health data indicative of physiological characteristics of the occupant based on the occupant-body signals, determine occupant state data indicative of a state of the occupant based on the occupant health data, and activate a first therapy system included in the plurality of therapy systems configured to change at least one physiological characteristic of the occupant based on at least one of the occupant health data and the occupant state data, and a backpack coupled to the comfort unit and the control system is located in the backpack, wherein the plurality of therapy systems include a ventilation system including a fan located in the backpack and configured to direct an air flow from the backpack through a ducting that extends through a bite line defined between a seat back and a seat bottom of the occupant support.

2. The health-monitoring cover of claim 1, wherein the control system is configured to activate a second therapy system included in the plurality of therapy systems based on at least one of the occupant health data, the occupant state data, and input from the occupant.

3. The health-monitoring cover of claim 1, wherein the control system is further configured to receive supplemental occupant-body signals after activating the first therapy system and determine a supplemental occupant health data based on the supplemental occupant-body signals.

4. The health-monitoring cover of claim 3, wherein the supplemental occupant health data includes an occupant presence, a heart rate of the occupant, a respiration rate of the occupant, and a blood pressure of the occupant.

5. The health-monitoring cover of claim 1, wherein the plurality of therapy systems includes a massage system, the ventilation system, and a heating system.

6. The health-monitoring cover of claim 5, wherein the massage system includes at least one pneumatic bladder.

7. The health-monitoring cover of claim 6, wherein the heating system includes a heat mat.

8. The health-monitoring cover of claim 7, wherein the comfort unit further includes a venting air channel layer, the at least one pneumatic bladder is located between the outer layer and the inner layer of the comfort unit, the heat mat is located between the at least one pneumatic bladder and the inner layer, the venting air channel layer is located between the heat mat and the inner layer, and the sensor system is located between the venting air channel layer and the inner layer.

9. The health-monitoring cover of claim 7, wherein the heat mat is formed to include a plurality of air flow openings configured to receive the at least one pneumatic bladder.

10. A health-monitoring cover comprising a comfort unit configured to couple removably to an occupant support that includes a seat bottom and a seat back, a sensor system coupled to the comfort unit, the sensor system configured to obtain occupant-body signals associated with physiological characteristics of an occupant of the occupant support, a control system configured to receive the occupant-body signals and determine occupant health data indicative of physiological characteristics of the occupant based on the occupant-body signals, and a backpack coupled to the comfort unit and the control system is located in the backpack, wherein the comfort unit includes a top cover that is arranged to lie on top of a forward surface of the seat back and the backpack is arranged to lie on a rear surface of the seat back, wherein the seat back of the occupant support is located between the top cover and the backpack, and a plurality of therapy systems integrated into the comfort unit and configured to relieve the occupant, wherein the plurality of therapy systems include a ventilation system including a fan located in the backpack and configured to direct an air flow from the backpack through a ducting that extends through a bite line defined between a seat back and a seat bottom of the occupant support.

11. The health-monitoring cover of claim 10, wherein the control system is configured to determine occupant state data indicative of a state of the occupant based on the occupant health data.

12. The health-monitoring cover of claim 11, wherein the control system is configured to activate the plurality of therapy systems based on at least one of the occupant health data and the occupant state data.

13. The health-monitoring cover of claim 12, wherein the plurality of therapy systems includes a massage system including a pneumatic bladder, the ventilation system, and a heat mat, the comfort unit includes an inner layer, a venting air channel layer, and an outer layer arranged over the inner layer and the venting air channel layer, the pneumatic bladder is located between the outer layer and the inner layer, the heat mat is located between the pneumatic bladder and the inner layer, the venting air channel layer is located between the heat mat and the inner layer, and the sensor system is located between the venting air channel layer and the inner layer.

14. The health-monitoring cover of claim 10, wherein the control system is further configured to identify the occupant based on at least one of input from the occupant and the occupant health data and to associate the occupant health data with a unique occupant data profile for the identified occupant.

15. The health-monitoring cover of claim 14, wherein the control system is configured to activate the plurality of therapy systems based on the occupant health data, and the control system is configured to associate activation of the plurality of therapy systems with the occupant health data in the unique occupant data profile.

* * * * *